(12) United States Patent
Rusler

(10) Patent No.: US 7,670,516 B2
(45) Date of Patent: Mar. 2, 2010

(54) DENTAL PROSTHETIC

(75) Inventor: Robert L. Rusler, Fairland, IN (US)

(73) Assignee: Indiana Dental Prosthetics, Inc., Indianapolis, IN (US)

( * ) Notice: Subject to any disclaimer, the term of this patent is extended or adjusted under 35 U.S.C. 154(b) by 318 days.

(21) Appl. No.: 11/673,770

(22) Filed: Feb. 12, 2007

(65) Prior Publication Data

US 2007/0190488 A1    Aug. 16, 2007

Related U.S. Application Data

(60) Provisional application No. 60/773,142, filed on Feb. 13, 2006.

(51) Int. Cl.
*A61C 13/10* (2006.01)

(52) U.S. Cl. .............. 264/18; 264/16; 264/17; 433/171; 433/172; 433/196; 433/199.1; 433/213; 523/120

(58) Field of Classification Search ............ 264/16, 264/17, 18, 19; 433/171, 172, 196, 199.1, 433/213; 523/120
See application file for complete search history.

(56) References Cited

U.S. PATENT DOCUMENTS

| | | | |
|---|---|---|---|
| 1,754,058 A * | 4/1930 | Smith ............ | 433/199.1 |
| 2,229,780 A * | 1/1941 | Vaillancourt ............ | 433/196 |
| 3,567,806 A | 3/1971 | Dyal | |
| 3,644,996 A | 2/1972 | Weinkle | |
| 3,846,911 A | 11/1974 | Wichner | |
| 4,012,838 A * | 3/1977 | Abdenour ............ | 433/171 |
| 4,017,971 A | 4/1977 | Hazar | |
| 4,097,992 A | 7/1978 | Hazar | |
| 4,175,322 A | 11/1979 | Tureaud | |
| 4,184,253 A | 1/1980 | Tureaud | |
| 4,195,047 A * | 3/1980 | Drennan et al. ............ | 264/17 |
| 4,337,042 A | 6/1982 | von Nostitz | |
| 4,457,713 A | 7/1984 | Schneider | |
| 4,470,815 A | 9/1984 | Hazar | |
| 4,517,043 A | 5/1985 | Martin et al. | |
| 4,521,193 A | 6/1985 | Cialone | |
| 4,533,325 A | 8/1985 | Blair et al. | |
| 4,583,947 A | 4/1986 | Hazar | |
| 4,705,476 A | 11/1987 | Blair | |
| 4,854,875 A | 8/1989 | Dziki et al. | |
| 5,304,062 A | 4/1994 | Saitoh et al. | |
| 5,502,087 A | 3/1996 | Tateosian et al. | |
| 5,554,665 A * | 9/1996 | Tateosian et al. ............ | 522/30 |
| 6,224,375 B1 * | 5/2001 | Diasti et al. ............ | 433/213 |
| 2002/0163096 A1 * | 11/2002 | Price ............ | 264/16 |

* cited by examiner

*Primary Examiner*—Joseph S Del Sole
*Assistant Examiner*—Timothy Kennedy
(74) *Attorney, Agent, or Firm*—Woodward, Emhardt, Moriarty, McNett & Henry LLP

(57) ABSTRACT

A system of manufacturing a custom set of pre-manufactured upper and lower dentures is provided. In one form, a set of master upper and lower dentures is created. The master upper and lower dentures are used to create reusable upper and lower dental matrices, respectively. These re-usable upper and lower dental matrices are repeatedly used to manufacture upper and lower pre-manufactured or standard sized dentures, respectively. Optionally, a dental patient can have these upper and lower pre-manufactured dentures custom fit or relined to fit the dental patient's mouth to form upper reline and/or lower reline pre-manufactured dentures. The dental patient can have custom fit dentures in two visits with the dentist, even two visits in the same day.

13 Claims, 19 Drawing Sheets

DENTAL PROSTHETIC

CROSS REFERENCE TO RELATED APPLICATION

This application claims the benefit of U.S. Provisional Patent Application No. 60/773,142 filed Feb. 13, 2006, which is hereby incorporated by reference in its entirety.

FIELD OF THE INVENTION

This invention relates generally to dentures, and more particularly to a method of manufacturing dentures.

BACKGROUND OF THE INVENTION

One method of manufacturing a custom set of dentures includes multiple visits between a patient and a dentist. The dentist typically sends the dentures multiple times at various stages in the manufacturing process to a dental laboratory for a technician to work on the dentures. For example, a dentist may take an impression of gums of a patient with a stock tray and send the impression to a technician for fabrication of custom trays from the impressions. Next, the dentist would receive the custom trays from the dental laboratory and take another impression of the arch or gums and send this impression to the dental laboratory. The technician at the laboratory constructs a base plate with bite rims and sends it back to the dentist for the dentist to determine the upper and lower bite relation. Then the dentist sends the base plate and bite rim back to the dental laboratory to set prosthetic teeth in wax. Typically after the dentist has fitted the dentures in the patient's mouth to check the bite and prosthetic teeth arrangement, the dentist would again send the dentures to a dental laboratory to process and finish. After processing and finishing the dentures, the dentures are sent back to the dentist for delivery to the patient. The time required for multiple visits between the patient and dentist and the time for labor on the custom dentures at the dental laboratory can be substantial and costly. Additionally, custom dentures can be costly since each set of dentures is custom made for a particular patient using that patient's arch to form the impressions and trays.

The present invention provides improvements for dentures and methods of manufacturing dentures.

DESCRIPTION OF PREFERRED EMBODIMENTS

For the purposes of promoting an understanding of the principles of the invention, reference will now be made to the embodiments illustrated and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention provides a method for manufacturing pre-manufactured or standard sized upper and lower dentures that may be fitted to a particular patient's mouth. The pre-manufactured upper and lower dentures facilitate the speed and convenience of creating fitted dentures. The first stage involves a method of manufacturing a master upper denture and a master lower denture. The master upper denture and the master lower denture may be used numerous times to ultimately fabricate one or multiple dental jigs or matrices. Further, the master lower denture and master upper denture determine the approximate size of the pre-manufactured lower and upper dentures. The second stage includes a method of manufacturing or fabricating a dental jig or matrix using the master upper denture and the master lower denture. The third stage includes a method of manufacturing a pre-manufactured or standard sized denture using the dental jig or matrix. The dental matrix may be used numerous times to create numerous pre-manufactured dentures. Preferably, the fourth stage includes custom fitting or "relining" the pre-manufactured dentures to fit a patient's gums. The master dentures, dental jig or matrix, and pre-manufactured dentures may be used in different embodiments and variations.

Creating Master Dentures

Figure 1:
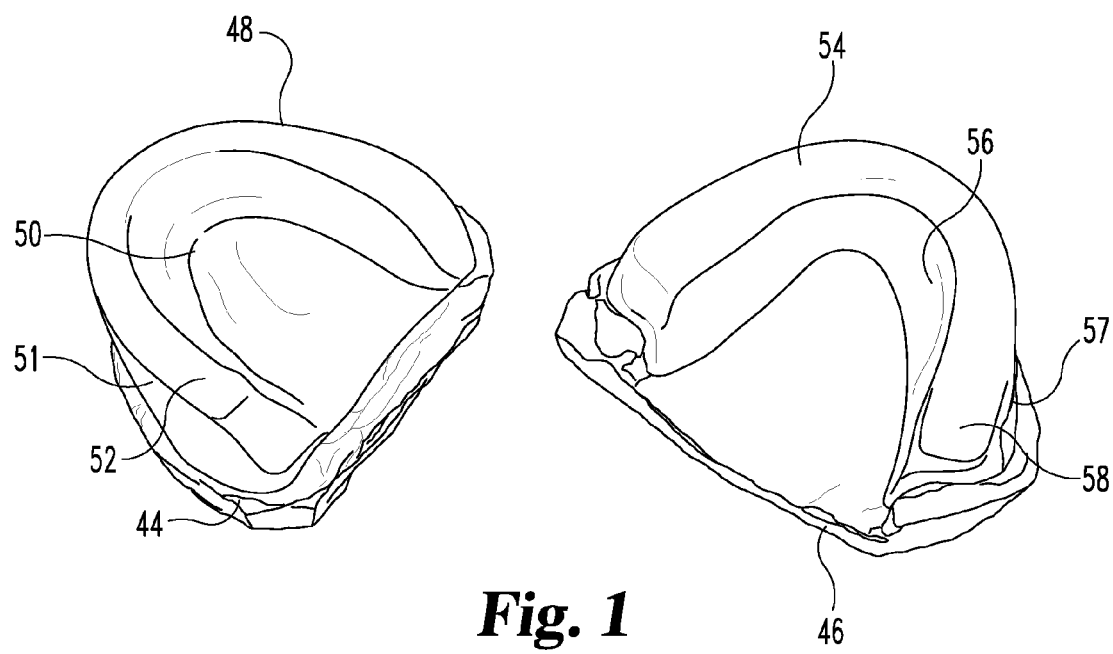
FIGS. 1-15 are perspective views of one embodiment of a method of manufacturing master dentures.
Figure 15:
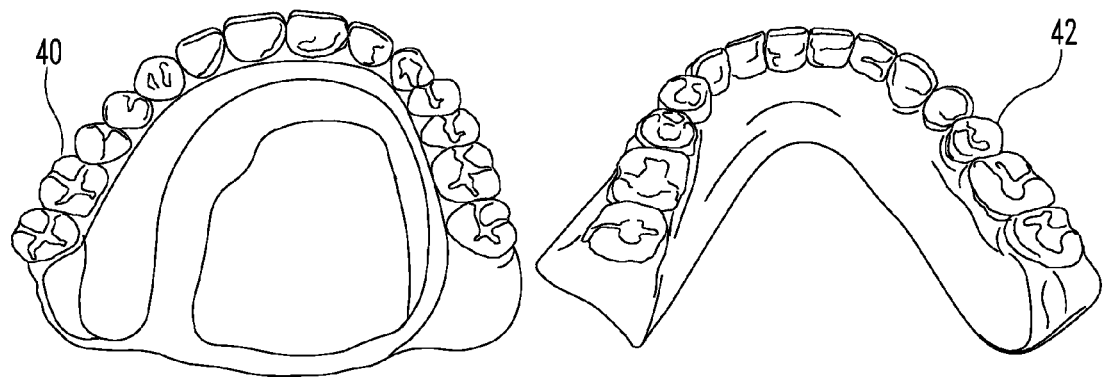

A master upper denture 40 and a master lower denture 42, as shown in FIG. 15, will be described. In this embodiment, the master upper denture 40 and the master lower denture 42 are fabricated similarly with differences described below; however, the master upper denture 40 will be described in detail. FIG. 1 illustrates an upper model 44 and a lower model 46. A user or processor, such as a dental technician, places an upper arch piece 48 onto the upper model 44. The upper arch piece 48 includes an upper base plate 50, an upper buccal flange 51, and an upper bite rim 52. A dental technician places a lower arch piece 54 onto the lower model 46. The lower arch piece 54 includes a lower base plate 56, a lower buccal flange 57, and a lower bite rim 58. In one embodiment, the upper base plate 50, upper buccal flange 51, upper bite rim 52, lower base plate 56, lower buccal flange 57, and lower bite rim 58 are made of wax. In a second embodiment, the upper base plate 50 and the lower base plate 56 are made of thermoplastic, and the upper buccal flange 51, upper bite rim 52, lower buccal flange 57, and lower bite rim 58 are made of wax. In other embodiments, the upper base plate 50, upper buccal flange 51, upper bite rim 52, lower base plate 56, lower buccal flange 57, and lower bite rim 58 are made of other materials.

Figure 2:
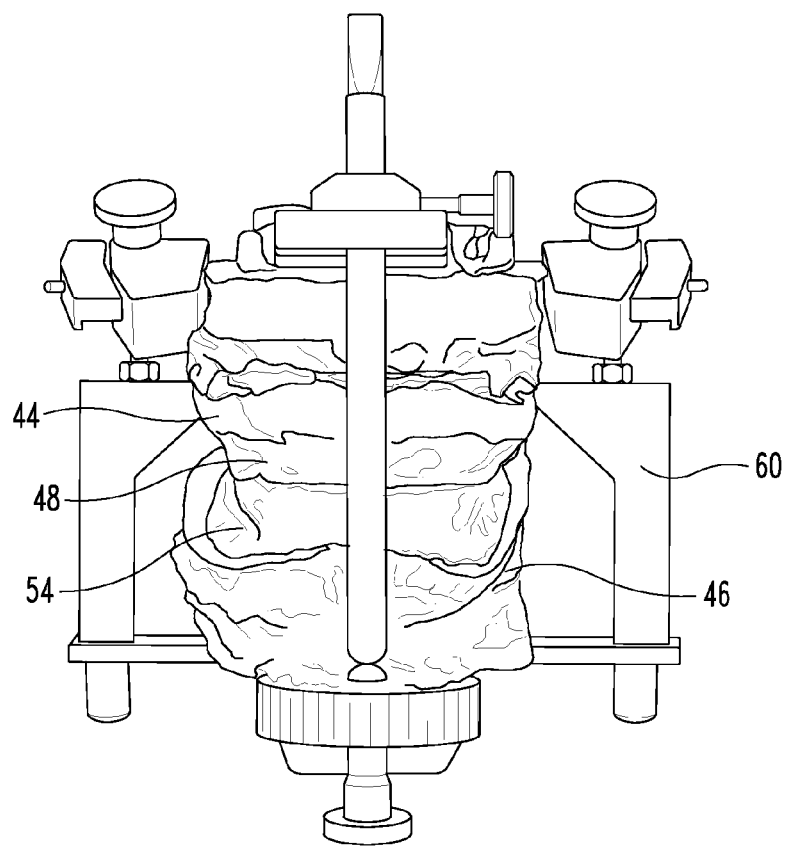

Next, as shown in FIG. 2, the upper model 44 with the upper arch piece 48 is placed into an articulator 60. In other embodiments, other forms of articulator 60 can be used. In this form, the articulator 60 duplicates the lower jaw movement of a person, and the articulator 60 holds the position of a person's natural bite. The articulator 60 also maintains the space vertically between the upper model 44 and the lower model 46. The dental technician uses a predetermined vertical length to position the upper arch piece 48 a distance from the lower arch piece 54. In one embodiment, the predetermined vertical length is approximately 15 mm; however, in other embodiments this length may be different. The articulator 60 holds the upper arch piece 48 and the lower arch piece 54 in alignment such that a dental technician or other person may properly place and align prosthetic teeth 62 in the upper base plate 50 and the lower base plate 56 as described below.

Figure 3:
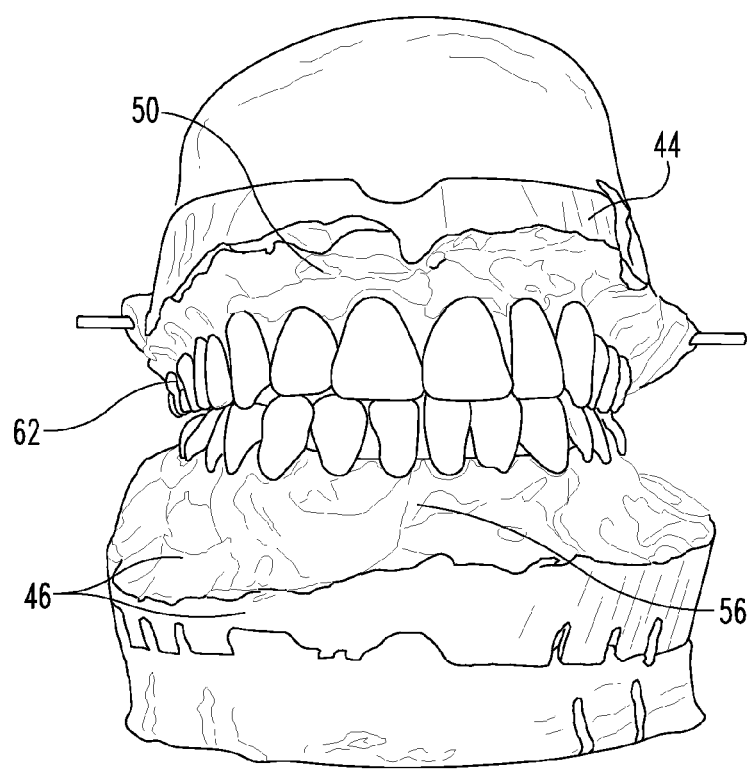
Figure 4:
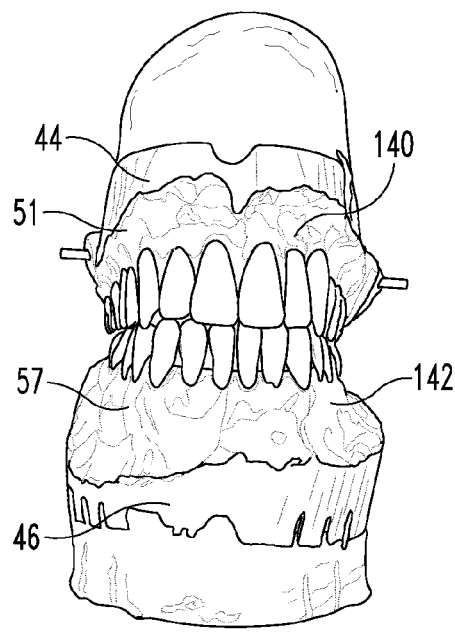

After the upper model 44 and the lower model 46 are placed in the articulator 60, prosthetic teeth 62 are set into the upper base plate 50 and the lower base plate 56 and adjusted or placed in their proper relation to each other, as shown in FIG. 3. In other embodiments, a whole or a partial arch of prosthetic teeth are set into the upper base plate 50 and/or the lower base plate 56. Wax is then added to the upper buccal flange 51 and to the lower buccal flange 57, as shown in FIG. 4, to form a wax setup upper denture 140 and a wax setup lower denture 142, respectively. As should be appreciated, the wax setup upper denture 140 and the wax setup lower denture 142 can be made in various sizes and shapes to accommodate persons with different sizes and shapes of oral cavities.

The upper model 44 and the lower model 46 are removed from the articulator 60. Next, the wax setup upper denture 140 is removed from the upper model 44, and the wax setup lower denture 142 is removed from the lower model 46.

Figure 5:
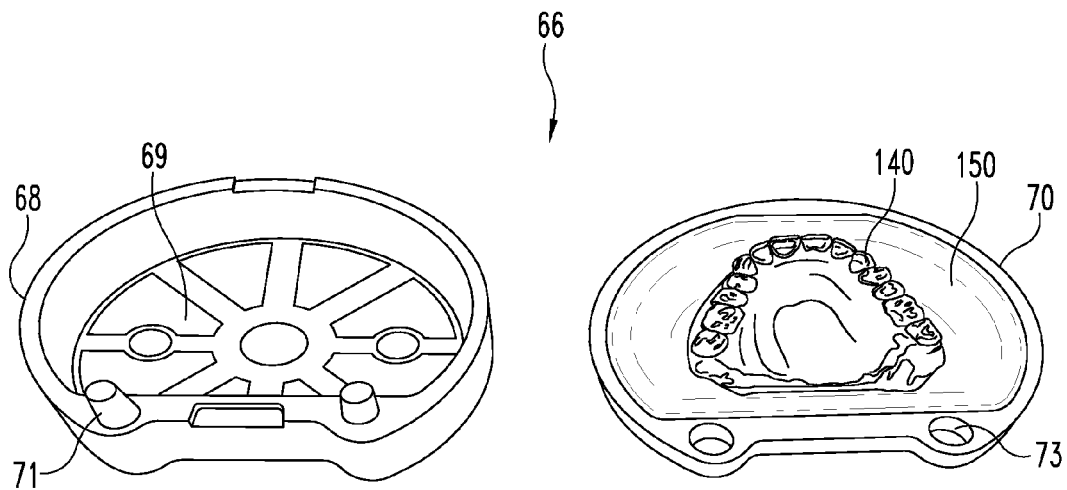

A denture flask 66 having a middle flask portion 68, a removable top portion 69, and a lower flask portion 70 is shown in FIG. 5. The top portion 69 may be removed from the middle flask portion 68, and the middle flask portion 68 is placed on the lower flask portion 70. In this form, the middle flask portion 68 includes a pair of guide pins 71, and the lower flask portion 70 includes a pair of holes 73 sized to receive the guide pins 71. In one form, fluent dental plaster 150 is placed in the lower flask portion 70, and the wax setup upper denture 140 is placed into the fluent or soft dental plaster 150. Preferably, the wax setup upper denture 140 is placed near or in the center of lower flask portion 70. Over a period of time, the dental plaster 150 sets until it is hard. In other embodiments, a denture container is configured to contain the wax setup upper denture 140 or other dental prosthetics.

Figure 6:
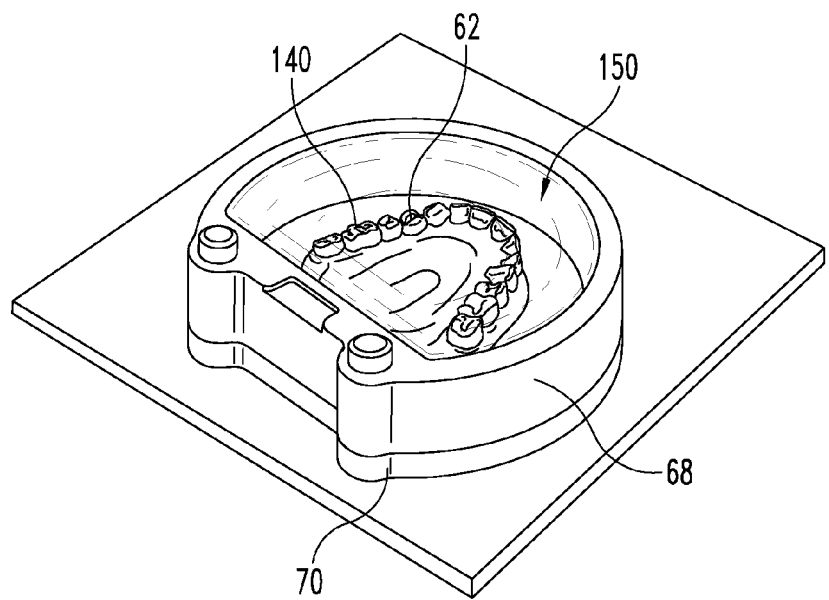

As shown in FIG. 6, the removable top portion 69 is removed from the middle flask portion 68, and the middle flask portion 68 is placed on top of the lower flask portion 70. Additional dental plaster 150 is poured over the wax setup upper denture 140 and the prosthetic teeth 62 until the middle flask portion 68 is filled with dental plaster. Preferably, the middle flask portion 68 is filled with dental plaster 150 to the outer edge and to the top of the middle flask portion 68. Optionally, the top portion 69 can be placed on top of the middle flask portion 68. Over a period of time, the dental plaster 150 sets until it is hard.

Figure 7:
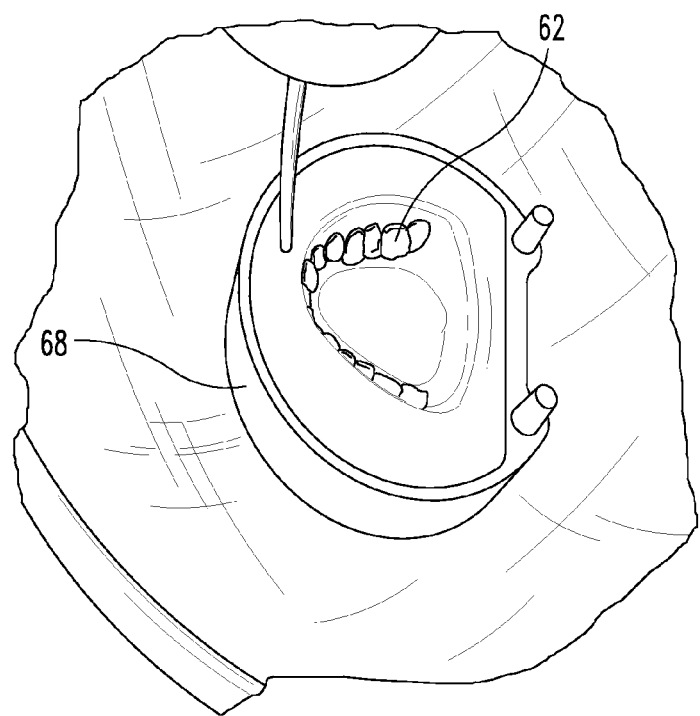
Figure 8:
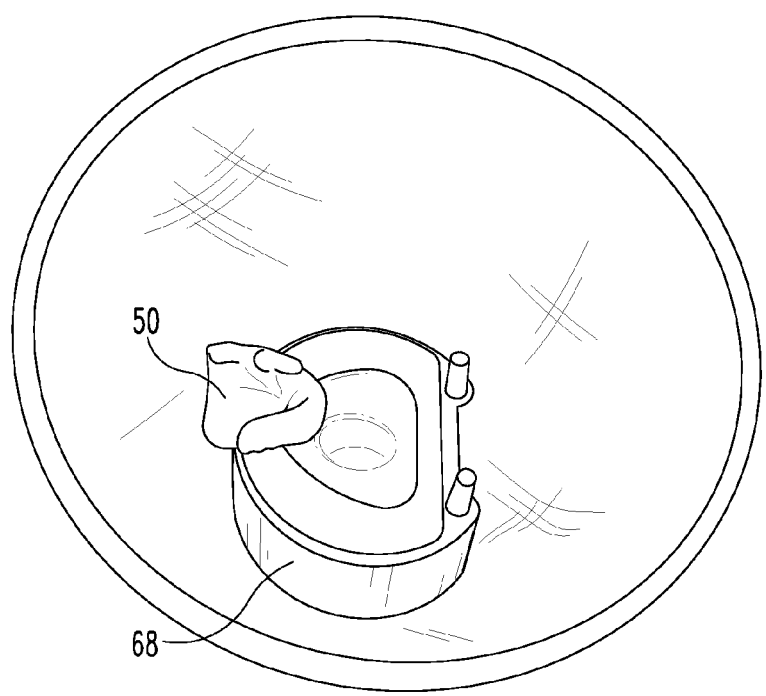

Next, the denture flask 66 is placed in boiling water for approximately five minutes. The denture flask 66 is separated into the middle flask portion 68 and the lower flask portion 70. In FIG. 7, boiling water is poured over the dental plaster to remove the wax and the upper base plate 50 from the middle flask portion 68 leaving an impression in the plaster. In FIG. 8, the upper base plate 50 is removed from the middle flask portion 68. Preferably, the prosthetic teeth 62 remain embedded in the dental plaster and positioned with the biting surface of each tooth upright or facing up. The denture flask 66 is allowed to cool.

Figure 9:
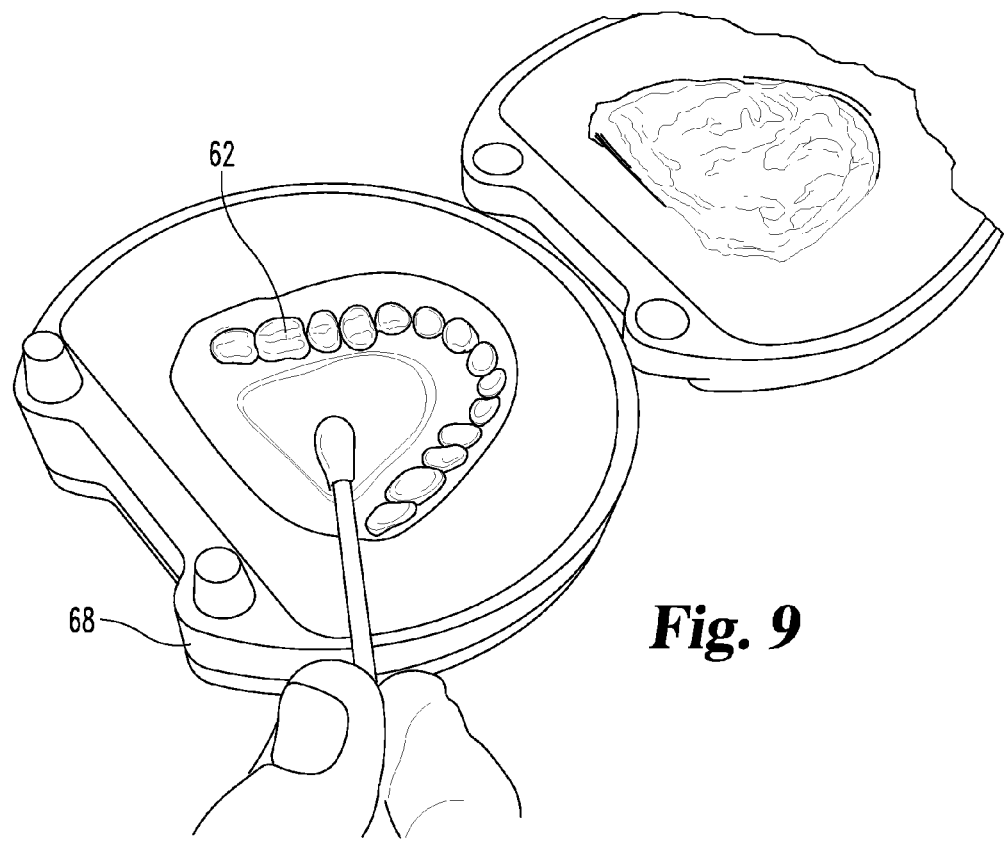
Figure 10:
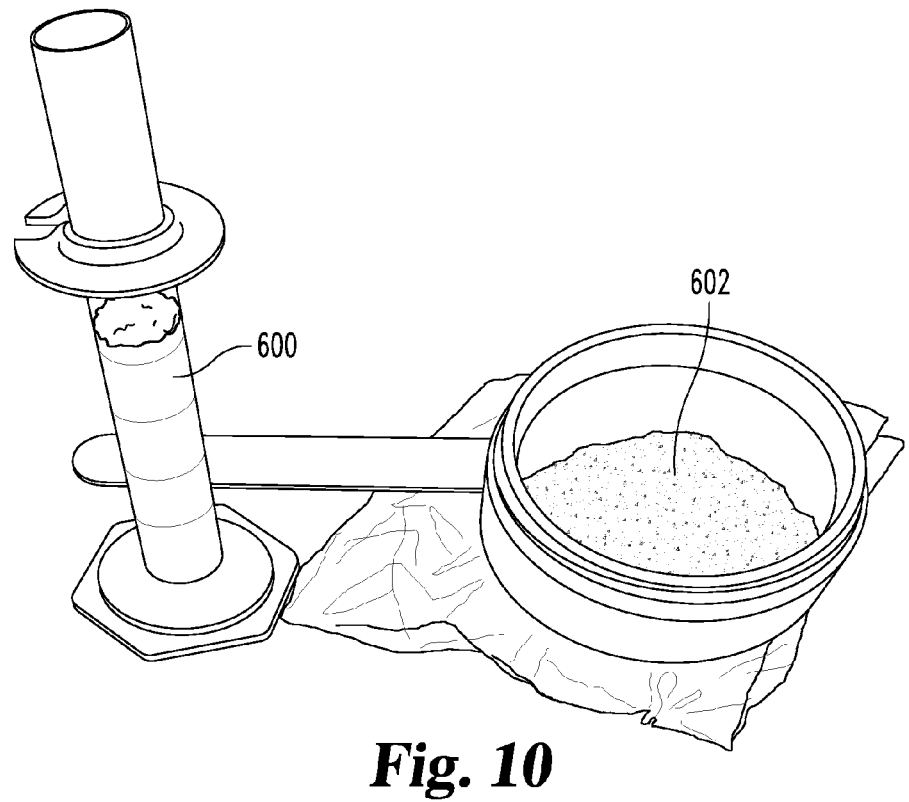
Figure 11:
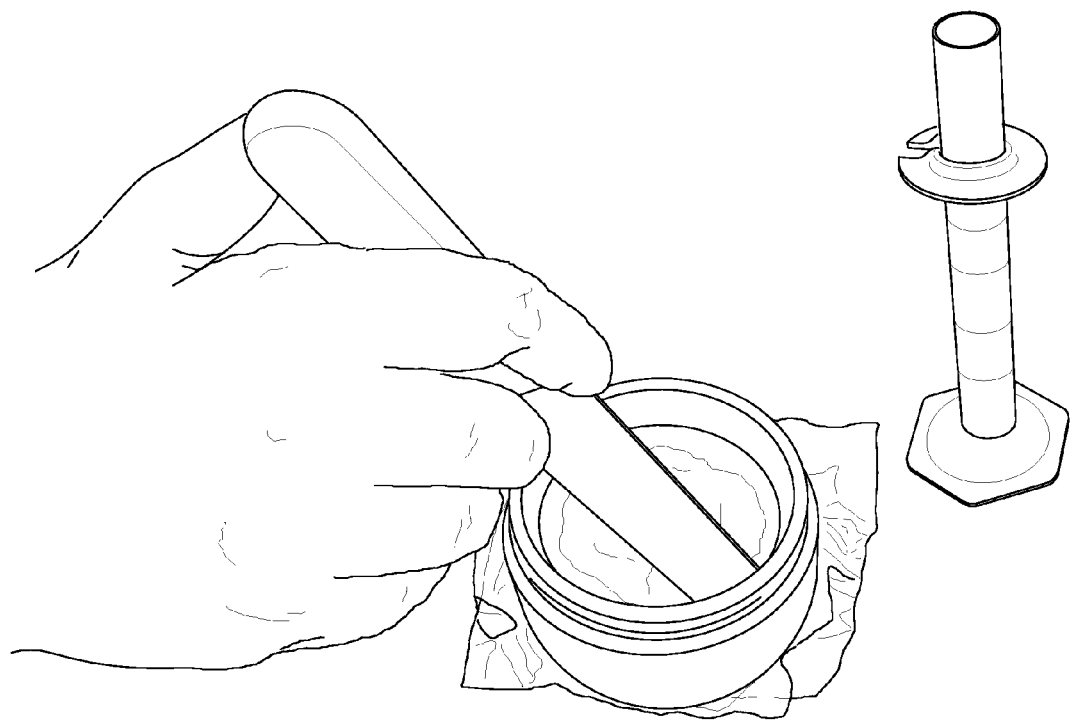
Figure 12:
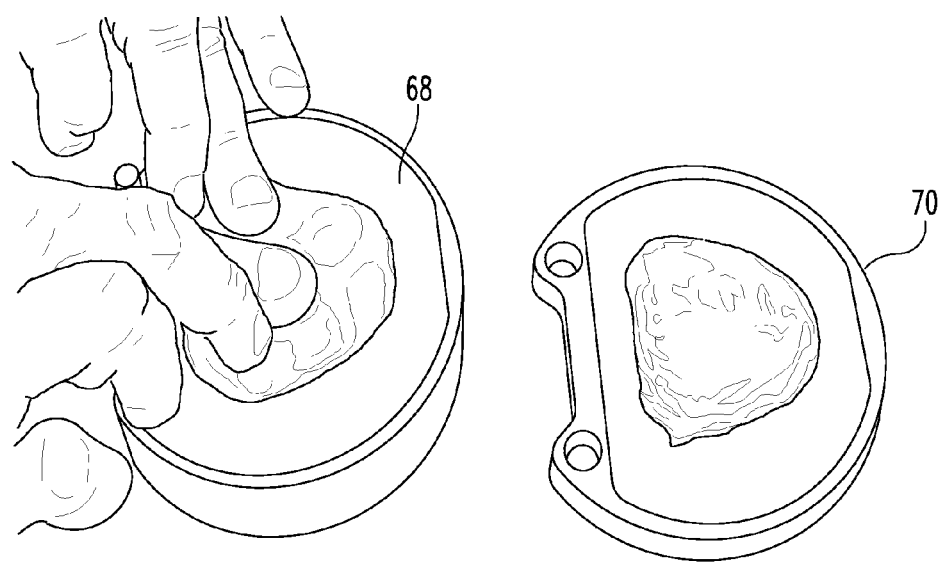
Figure 13:
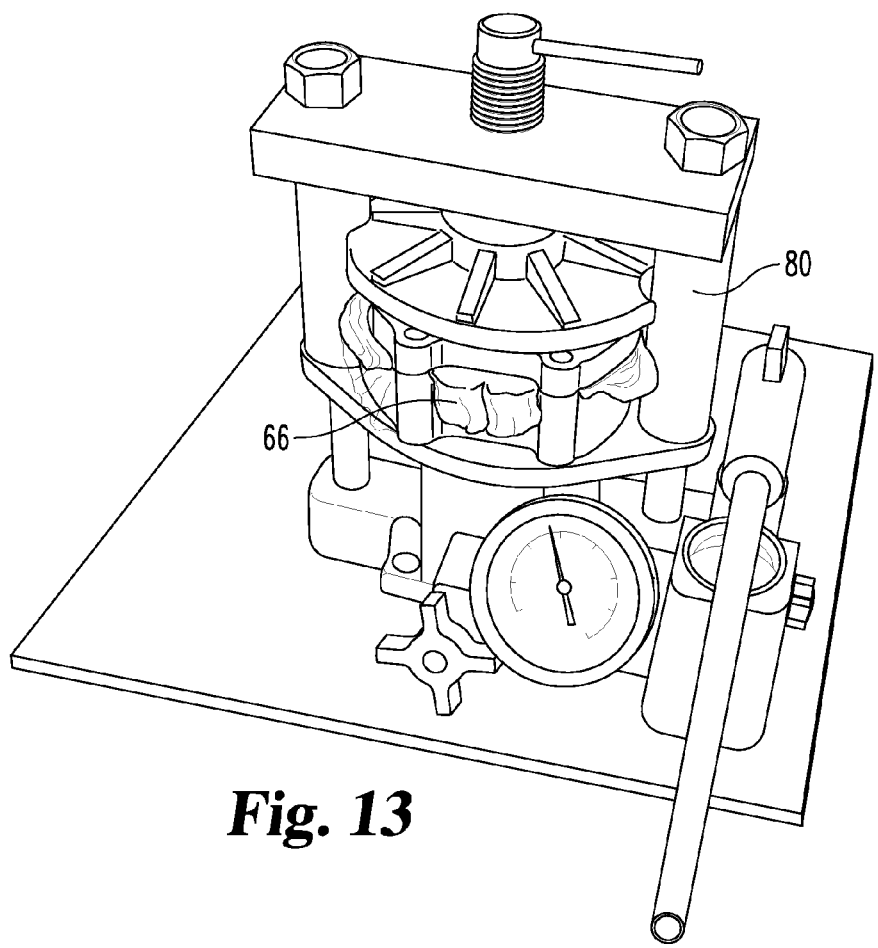

As shown in FIG. 9, the prosthetic teeth 62 are cleansed to remove remaining wax. In one embodiment, monomer on a cotton swab may be used to clean prosthetic teeth 62; however, in other embodiments, other substances may be used to clean prosthetic teeth 62. Next, the master upper denture 40 is formed. First, an amount of acrylic 600 and an amount of monomer 602 are measured as shown in FIG. 10 and mixed together to form a doughy material as shown in FIG. 11. The acrylic 600 and monomer 602 are mixed together and stirred, as shown in FIG. 11, until a pliable or doughy state is reached. In one embodiment, the acrylic 600 and monomer 602 are stirred for about five minutes to reach a pliable or doughy state. The doughy material is placed in the middle flask portion 68 that contains prosthetic teeth 62 as shown in FIG. 12. In other embodiments, the doughy material is injected into the middle flask portion 68 to form the master upper denture 40. In one form, approximately 8 cubic centimeters of monomer and approximately 27 cubic centimeters of acrylic are measured. However, in other embodiments, the amount of monomer 602 and the amount of acrylic 600 may be different. The middle flask portion 68 is placed on top of the lower flask portion 70. The denture flask 66 is placed into a denture press 80 wherein the middle flask portion 68 and the lower flask portion 70 are closed together as shown in FIG. 13. The denture press 80 applies pressure to the denture flask 66 to squeeze any excess acrylic out of the denture flask 66.

Figure 14:
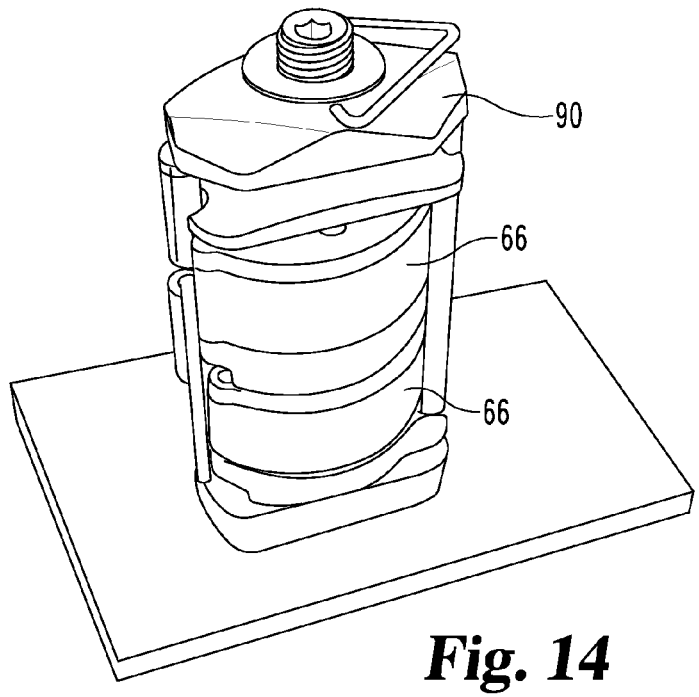

The denture flask 66 is removed from the denture press 80, and the denture flask 66 is placed into a compress 90 as illustrated in FIG. 14. In this illustration, two denture flasks 66 are placed in the compress 90; however, in other embodiments, a different number of denture flasks 66 can be placed on the compress 90. The compress 90 maintains a certain pressure on the dental flask 66 while the acrylic cures, which reduces the porosity of the acrylic. The compress 90 is typically placed in a curing unit to cure the acrylic. Often, the curing unit is a hot water bath. After the curing is complete, the middle flask portion 68 is removed from the lower flask portion 70. The master upper denture 40 is removed from the middle flask portion 68.

In one embodiment, the master upper denture 40 is finished to remove any burrs, bubbles, or other imperfections from the acrylic. In one form, the imperfections in the acrylic surface of master upper denture 40 are removed with a felt-type wheel that is mounted on and rotated by a motor. In another form, the imperfections are removed with a wet pumice. Optionally, the master upper denture 40 is polished with denture polish placed on a rag wheel wherein the rag wheel is mounted to and rotated by a motor.

In FIG. 15, a master upper denture 40 and a master lower denture 42 are shown. The master upper denture 40 and the master lower denture 42 may be used to fabricate multiple dental jigs or dental matrices as described below.

Fabricating Dental Jig or Matrix

The second stage of manufacturing pre-manufactured dentures includes a method of manufacturing a dental jig or a dental matrix using either the master upper denture 40 or the master lower denture 42. The dental matrix is used to fabricate pre-made or standard sized dentures which may be fitted to a particular person's mouth as described below. A first method of manufacturing or fabricating an upper dental matrix 200 is described with reference to FIGS. 16, 17, 18, 19, and 20. In this stage, an upper dental matrix 200 from the master upper denture 40 and a lower dental matrix from the master lower denture 42 are fabricated similarly. Therefore, similar steps would be used to manufacture the lower dental matrix.

Figure 16:
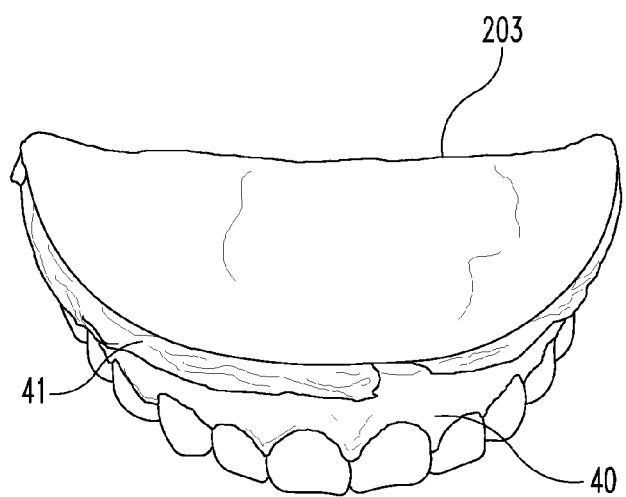
FIGS. 16-20 are perspective views of one embodiment of a method of manufacturing a dental jig.
Figure 17:
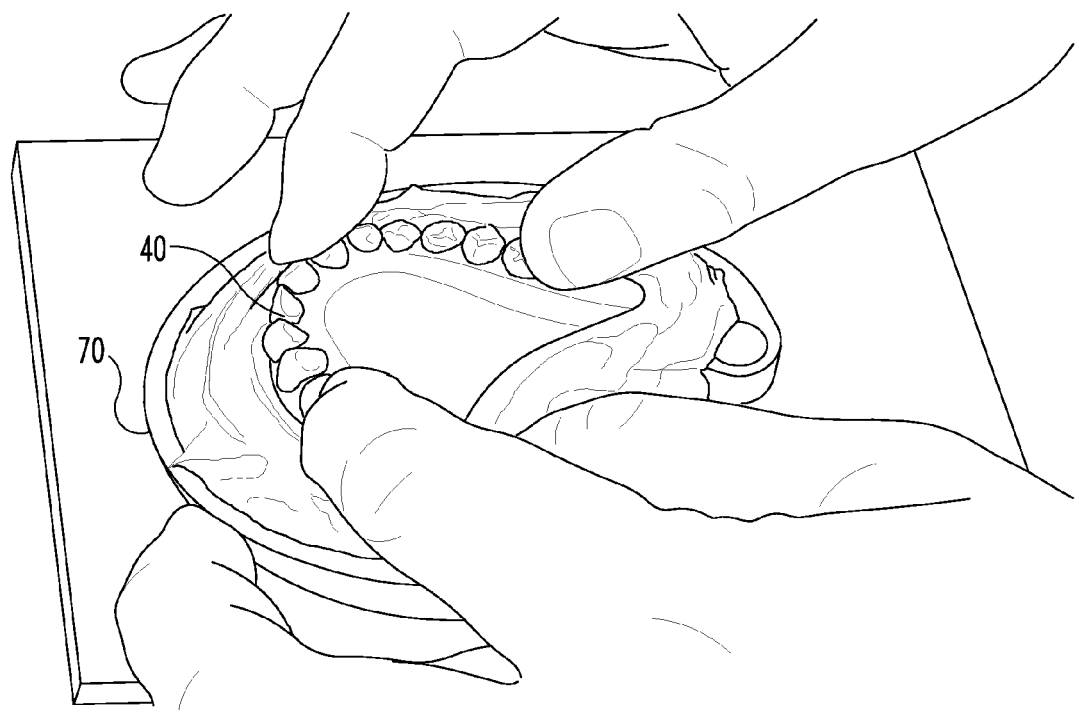

First, impression material 203 is packed into the master upper denture 40 on a tissue side 41 as shown in FIG. 16. In one form, the impression material 203 is made of vinyl polysiloxane or any polymeric siloxane, particularly silicone. However, in other forms, impression material 203 is any type of durable, flexible material. Dental stone, fluent curable dental plaster, or fluent curable dental material is placed in the lower flask portion 70 of the denture flask 66. The master upper denture 40 is placed tissue side down in or near the center of the lower flask portion 70 as shown in FIG. 17.

Figure 18:
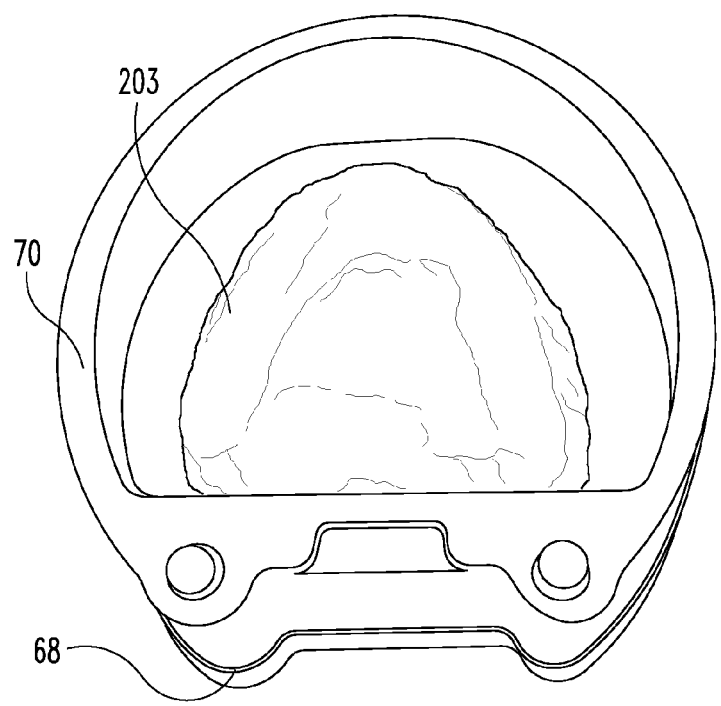

As shown in FIG. 18, impression material 203 is placed on the master upper denture 40. Preferably, the impression material 203 covers prosthetic teeth 62, upper buccal flange 51, and the center area or palate of the master upper denture 40. In this form, impression material 203 is vinyl polysiloxane; however, other materials can be used.

Figure 19:
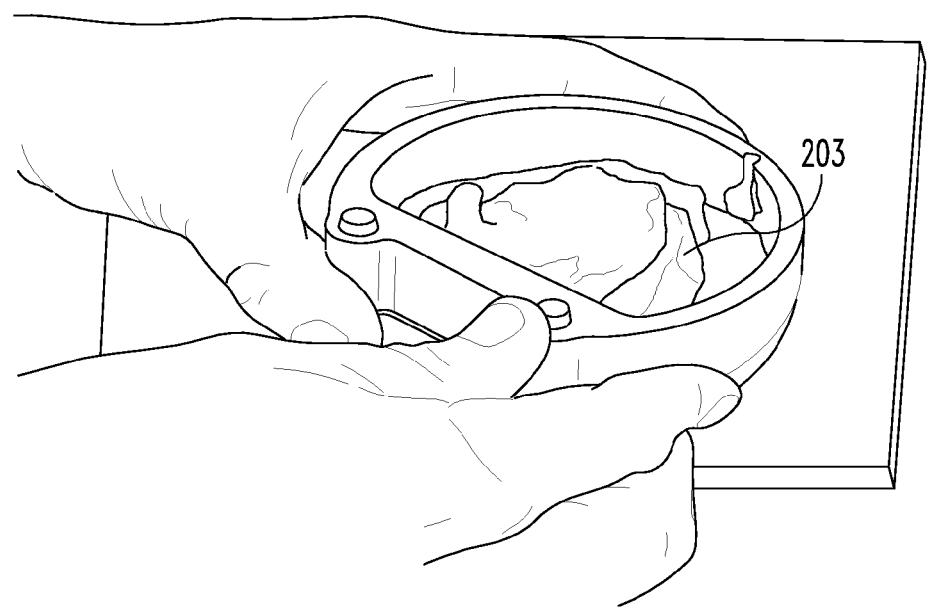

The middle flask portion 68 of the denture flask 66 is placed on the lower flask portion 70, and dental stone or fluent curable dental material is placed around the prosthetic teeth 62 and over the top of the master upper denture 40 as shown in FIG. 19 to fill the lower flask portion 70. After a period of time, the dental stone or dental material hardens.

Figure 20:
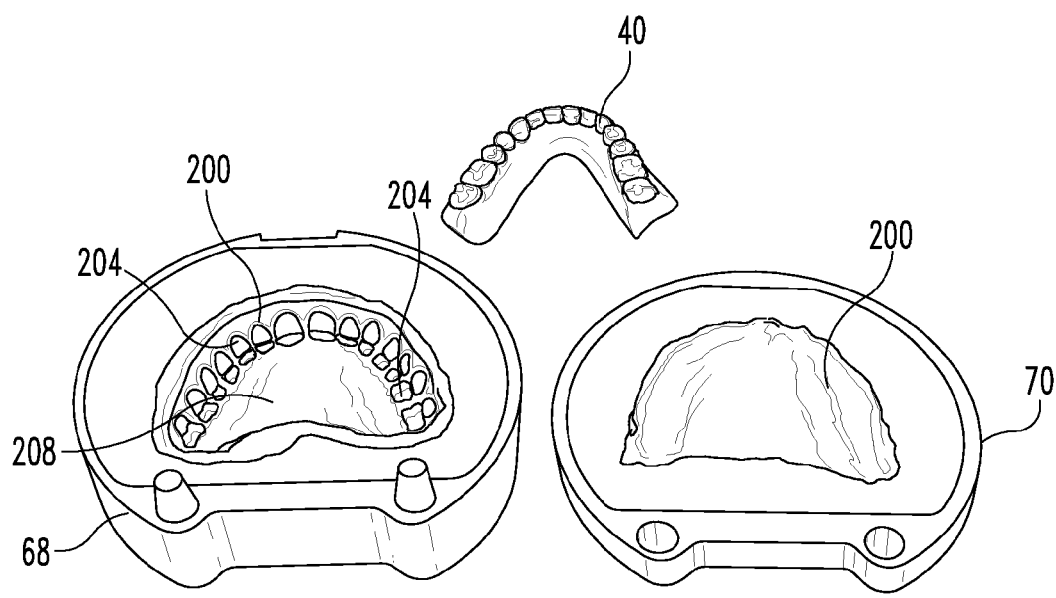

The denture flask 66 is separated into the middle flask portion 68 and the lower flask portion 70, and the master upper denture 40 is removed from the denture flask 66 as shown in FIG. 20. As shown in FIG. 20, the upper denture 40 does not include a palate. The upper dental matrix 200 remains in the denture flask 66, having been formed from the impression material 203 in the lower flask portion 70 and the impression material 203 in the middle flask portion 68. The upper dental matrix 200 includes impressions 204 of prosthetic teeth 62 from the master upper denture 40. The upper dental matrix 200 also includes a mold 208 of the center or palate area of the master upper denture 40. Similarly, lower dental matrix of the master lower denture 42 will include a mold of the lower denture 42 and impressions of prosthetic teeth 62 from the master lower denture 42.

The upper dental matrix 200 and the lower dental matrix may be used to create an upper pre-manufactured or standard sized denture 300 and a lower pre-manufactured or standard sized denture, respectively. The upper dental matrix 200 and the lower dental matrix may be used until the impression material 203 degrades. In this form, a subsequent upper dental matrix 200 and/or lower dental matrix may be fabricated in the denture flask 66.

A second method of manufacturing or fabricating an upper dental matrix 500 is described with reference to FIGS. 21 and 22. Upper dental matrix 500 and a lower dental matrix may each be formed as part of a matrix tool 504 in which one or multiple upper pre-manufactured dentures 300 or lower pre-manufactured dentures may be manufactured. Manufacturing multiple upper or lower pre-manufactured dentures in one step increases production of the pre-manufactured dentures. In one embodiment, either upper dental matrix 500 or lower dental matrix forms three upper pre-manufactured dentures or three lower pre-manufactured dentures.

The finished upper pre-manufactured denture 300 will be used to describe the steps to manufacture the upper dental matrix 500. In other forms, the master upper denture 40 is used to manufacture the upper dental matrix 500. Similar steps are used to manufacture the lower dental matrix. Upper dental matrix 500 and lower dental matrix can be used to manufacture additional or subsequent pre-manufactured dentures.

Matrix tool 504 includes an upper plate 506 and a lower plate 508. Upper plate 506 is rectangular in shape; however, in other embodiments upper plate 506 can be shaped differently. For example, upper plate 506 can form a circular, a trapezoidal, or a triangular shape, to name a few. In one embodiment, a metal cast 509 of the upper pre-manufactured denture 300 is affixed to the upper plate 506 to form an upper prosthetic teeth portion 510. The metal cast 509 and upper plate 506 can be joined together by many techniques, such as, glue, welds, and/or fasteners, to name a few. In one embodiment, the metal cast 509 of upper pre-manufactured denture 300 is formed by a lost-wax casting technique. Additionally, in this embodiment, the metal cast 509 of upper pre-manufactured denture 300 and the upper plate 506 are cast together to affix the metal cast 509 to the upper plate 506 and form the upper prosthetic teeth portion 510. In this form, the metal cast 509 of upper pre-manufactured denture 300 and upper plate 506 are separate elements that are joined together. As should be appreciated, a plurality of casts 509 and/or a plurality of upper pre-manufactured dentures 300 can be attached to upper plate 506 to form a plurality of upper prosthetic teeth portions 510. Upper prosthetic teeth portion 510 includes a plurality of teeth 511. Preferably upper prosthetic teeth portion 510 has substantially the same dimensions as the master upper denture 40.

Figure 21:
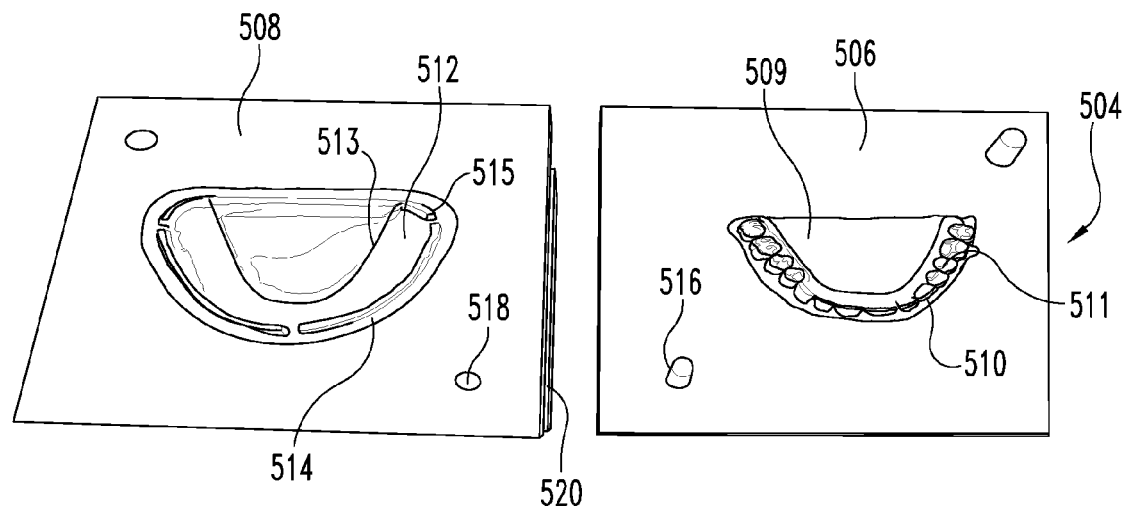
FIGS. 21 and 22 are perspective views of another embodiment of a method of manufacturing a dental jig.

As illustrated in FIG. 21, lower plate 508 is rectangular in shape and similarly sized as upper plate 506. In other embodiments, lower plate 508 can be shaped differently and sized differently from upper plate 506. For example, lower plate 508 can be circular, trapezoidal, or triangular in shape. Lower plate 508 includes a cavity 512 of similar size and shape as upper prosthetic teeth portion 510. Cavity 512 is shaped to receive upper prosthetic teeth portion 510. In one form, cavity 512 has a perimeter 513 that is approximately 2 or 3 millimeters larger than the perimeter of upper prosthetic teeth portion 510. In another form, lower plate 508 can include a plurality of cavities 512 such that each cavity 512 receives one upper prosthetic teeth portion 510. In the illustrated embodiment, lower plate 508 defines an overflow ridge 514 around cavity 512. Additionally, perimeter 513 includes a slot 515 between cavity 512 and overflow ridge 514. As illustrated, perimeter 513 includes three slots 515. In other embodiments, perimeter 513 can include a plurality of slots 515. In other embodiments, overflow ridge 514 may partially surround cavity 512. In one form, overflow ridge 514 has a "V" cross-sectional shape; however, in other embodiments, overflow ridge 514 can have a different cross-sectional shape. For example, overflow ridge 514 can have a rectangular, semi-circular, semi-oval, or trapezoidal cross-sectional shape.

In this embodiment, upper plate 506 includes a set of guide pins 516 and lower plate 508 defines a corresponding set of holes 518 configured to receive guide pins 516 such that upper prosthetic teeth portion 510 nests in cavity 512 and upper plate 506 is connected with lower plate 508. In other embodiments, lower plate 508 may contain a set of guide pins and upper plate 506 may define a corresponding set of holes. Other forms of connecting upper plate 506 with lower plate 508 and aligning upper prosthetic teeth portion 510 with cavity 512 may be used in other embodiments.

Optionally lower plate 508 defines a groove 520 at the edge of lower plate 508. Groove 520 is positioned adjacent upper plate 506 when lower plate 508 and upper plate 506 are assembled together. Groove 520 is positioned to enable a user to more easily separate upper plate 506 from lower plate 508 when lower plate 508 and upper plate 506 are assembled together. Further, in another embodiment, upper plate 506 defines a groove at the edge of upper plate 506 adjacent lower plate 508 when lower plate 508 and upper plate 506 are assembled together.

Upper plate 506 and lower plate 508 are formed from a material such as metal, plastic, or a composite material. In one embodiment, upper plate 506 and lower plate 508 are formed from aluminum. In another embodiment, upper plate 506 and lower plate 508 are formed from steel.

To finish manufacturing upper dental matrix 500, fluent curable impression material 517 is placed in cavity 512 in FIG. 21. In one embodiment, the fluent curable impression material 517 is silicone material. In one particular embodiment, the silicone material is a 50 durometer heat cure silicone. In other embodiments, the fluent curable impression material 517 can be plastic or metal and is placed in cavity 512 to form an impression of upper prosthetic teeth portion 510 as described next. Upper prosthetic teeth portion 510 is positioned in cavity 512 such that the fluent curable impression material 517 covers the prosthetic teeth 511. Each of guide pins 516 of upper plate 506 is positioned in one of holes 518 of lower plate 508 such that upper prosthetic teeth portion 510 nests in cavity 512 and upper plate 506 is connected with lower plate 508. Excess fluent curable impression material 517 is pushed or squeezed through slot 515 into overflow ridge 514 when upper plate 506 contacts lower plate 508. The fluent curable impression material 517 in cavity 512 hardens or cures to a solid form. In one embodiment, the fluent curable impression material 517 is heat cured to a firm and/or solid state.

Figure 22:
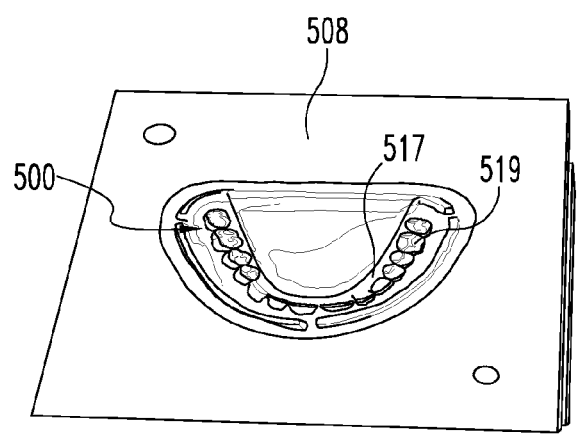

The upper plate 506 is separated from the lower plate 508 to form upper dental matrix 500, as illustrated in FIG. 22, and expose impressions 519 of prosthetic teeth 511 in the cured impression material. Upper dental matrix 500 is used similarly to upper dental matrix 200 to form pre-manufactured dentures as described below. However, upper dental matrix 500 and lower dental matrix are manufactured from materials that are resistant to degrading or wearing down with repeated use. Upper dental matrix 500 and lower dental matrix can be used repeatedly to fabricate pre-manufactured dentures or master dentures without necessarily re-fabricating upper dental matrix 500 or lower dental matrix. Also, upper dental matrix 500 and lower dental matrix can be used repeatedly to fabricate additional upper dental matrices and lower dental matrices, respectively.

Manufacturing Pre-Manufactured or Standard Sized Dentures

Figure 23:
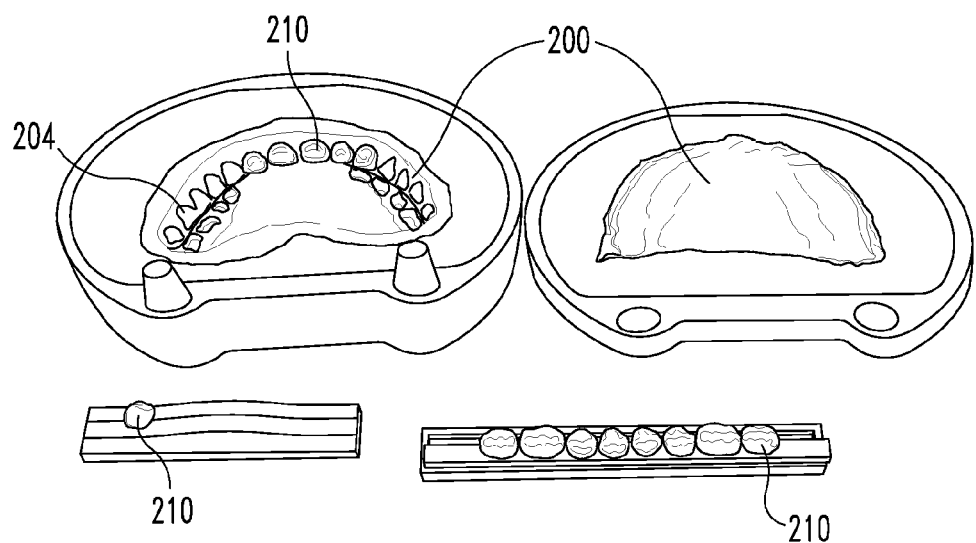
FIGS. 23 and 24 are perspective views of one embodiment of a method of manufacturing a pre-manufactured denture.

The third stage of manufacturing pre-manufactured dentures includes a method of manufacturing an upper pre-manufactured denture 300 and a lower pre-manufactured denture from a dental jig or matrix. The method is described with reference to FIGS. 23 and 24. Although the method is described with reference to upper dental matrix 200, the method is similarly applicable to lower dental matrix, upper dental matrix 500, and lower dental matrix, except as noted. As should be appreciated, a lower pre-manufactured denture is manufactured similarly as the upper pre-manufactured denture 300. As shown in FIG. 23, prosthetic teeth 210 are placed in the impressions 204 of the upper dental matrix 200. The prosthetic teeth 210 are positioned in the impression 204 with the biting surface of the tooth facing down or into the impression material 203 in upper dental matrix 200. Prosthetic teeth 210 are positioned in the impressions in upper dental matrix 500 with the biting surface of the tooth facing down; however, there is no impression material 203 in upper dental matrix 500. Instead, prosthetic teeth 210 rest against the cured impression material 517 in cavity 512. Preferably, prosthetic teeth 210 are of a similar size and similar shape as prosthetic teeth 62 used to form the impressions 204 in the upper dental matrix 200. However, prosthetic teeth 210 may be a different shade or color than prosthetic teeth 62. In other embodiments, prosthetic teeth 210 are part of or form a continuous arch of teeth. For example, prosthetic teeth 210 can be a series of teeth or a partial arch of teeth, a complete arch of teeth, and/or individual teeth.

The prosthetic teeth 210 are cleaned. Prosthetic teeth 210 may be cleaned similarly to the process described with reference to FIG. 9. In one embodiment, the prosthetic teeth 210 are cleaned with monomer. Next, an amount of acrylic and an amount of monomer are measured similar to the process described with reference to FIG. 10. The acrylic and monomer are mixed together and stirred until a doughy state is reached similar to the process described with reference to FIG. 11. In one form, the acrylic and monomer are stirred for about five minutes to reach a doughy state.

Next, the mixture of acrylic and monomer or doughy material is packed into the upper dental matrix 200 to cover the prosthetic teeth 210 and the mold 208 of the upper dental matrix 200. The lower flask portion 70 is inverted and placed on top of the middle flask portion 68. The denture flask 66 is placed into a denture press 80 to remove excess material wherein the middle flask portion 68 and the lower flask portion 70 are closed together similar to FIG. 13. Similarly, for upper dental matrix 500, the mixture of acrylic and monomer is packed into the lower plate 508 in cavity 512 over the cured impression material 517 to cover prosthetic teeth 210. A cover plate or other object is positioned on lower plate 508 to cover cavity 512. The cover plate and lower plate 508 are placed into denture press 80 to remove excess material as the denture press 80 squeezes the cover plate and lower plate 508 together. In some embodiments, excess material is squeezed into overflow ridge 514.

Figure 24:
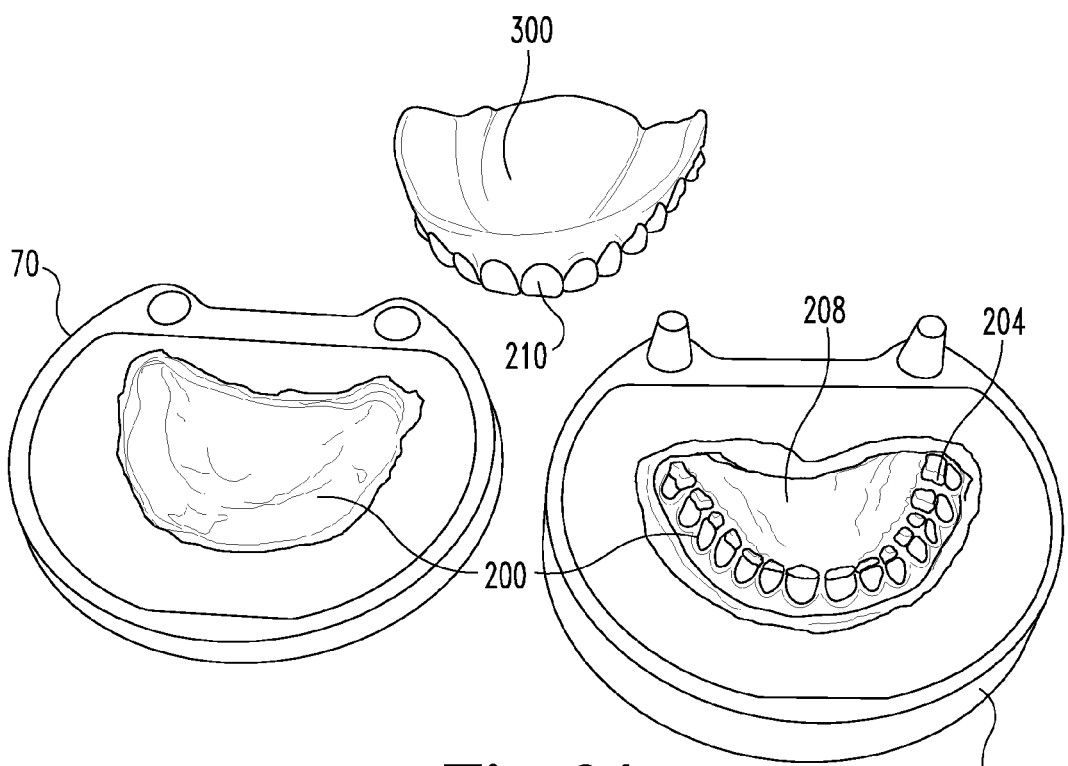

The denture flask 66 (or lower plate 508 and cover plate) are removed from the denture press 80, and the denture flask 66 is placed into a compress 90 similar to FIG. 14. The compress 90 is placed in a curing unit to cure the acrylic. After the curing is complete, the middle flask portion 68 is removed from the lower flask portion 70. The upper pre-manufactured denture 300 is removed from the middle flask portion 68 as shown in FIG. 24. Similarly, for upper dental matrix 500, after the curing is complete, the cover plate is removed from the lower plate 508 and the upper pre-manufactured denture 300 is removed from cavity 512.

After the upper pre-manufactured denture 300 is removed from the middle flask portion 68, a material 550 is placed on the tissue side of the upper base plate of the upper pre-manufactured denture 300 to form a substantially flat palate near the center of the upper base plate. As should be appreciated, one of the largest variations in dentures is the roof of a person's mouth. In one embodiment, the material 550 is wax or another flexible material, and in a second embodiment, the material is acrylic. For wax material or other flexible material, the dentist fits the material 550 to the roof of the person's mouth to reline the upper pre-manufactured denture, as described below.

Beneficially, the upper dental matrix 200 can be reused to form another upper pre-manufactured denture 300 until the impression material 203 that forms the upper dental matrix 200 degrades or is worn out. When the impression material 203 degrades, another upper dental matrix 200 or lower dental matrix may be formed in the denture flask 66 using the master upper denture 40 or the master lower denture 42.

Similarly, the upper dental matrix 500 can be reused to form upper pre-manufactured denture 300 without necessarily wearing down the cured impression material 517 in cavity 512. Beneficially, upper dental matrix 500 can also be used to manufacture a plurality of upper pre-manufactured dentures at one casting. Also beneficially, the upper dental matrix 500 can be used to form additional upper dental matrices. Moreover, the re-usability of upper dental matrix 500 may reduce the cost of fabricating dentures.

The lower pre-manufactured denture or the upper pre-manufactured denture 300 can be finished and polished similarly to the master upper denture 40. The upper pre-manufactured denture 300 can be sold to a dentist wherein the dentist may reline or modify the upper pre-manufactured denture 300 to custom fit an individual patient's arch and gums as described in more detail below. As should be appreciated, the upper pre-manufactured denture 300 can be made in various sizes and shapes using various sizes and shapes of master upper denture 40. The upper pre-manufactured denture 300 and lower pre-manufactured denture may reduce the number of visits to a dentist since the dentist may use the pre-made denture and fit it to a patient's mouth as described below. Additionally, the cost of fabricating the upper pre-manufactured denture 300 and lower pre-manufactured denture may be reduced if the methods discussed herein are practiced.

Relining Pre-manufactured Dentures

An optional fourth stage includes a method of relining or fitting the upper pre-manufactured denture 300 as described with reference to FIGS. 26, 27, 28, 29, 30, 31, 32, 33, 34, 35, 36, and 37. Relining the lower pre-manufactured denture is similar to the method described below of relining the upper pre-manufactured denture 300. The method of relining pre-manufactured dentures enables a dentist or dental technician to custom fit the upper and lower pre-manufactured dentures or other prefabricated dentures to a particular patient's mouth more quickly than traditional methods of fabricating custom dentures. Additionally, the method of relining pre-manufactured dentures requires fewer visits between the patient and dentist than traditional methods of fabricating custom dentures. Typically, a patient will be required to make two visits to a dentist's office to have upper pre-manufactured denture 300 and/or lower pre-manufactured denture custom fit to his mouth. In one form, a patient could visit a dentist in the morning and pick up his relined pre-manufactured dentures later in the same day or the next day.

At a patient's first visit, the dentist determines the color and size of an arch of a patient's mouth and chooses the color and size of the upper pre-manufactured denture 300 closest to the patient's arch.

Figure 25:
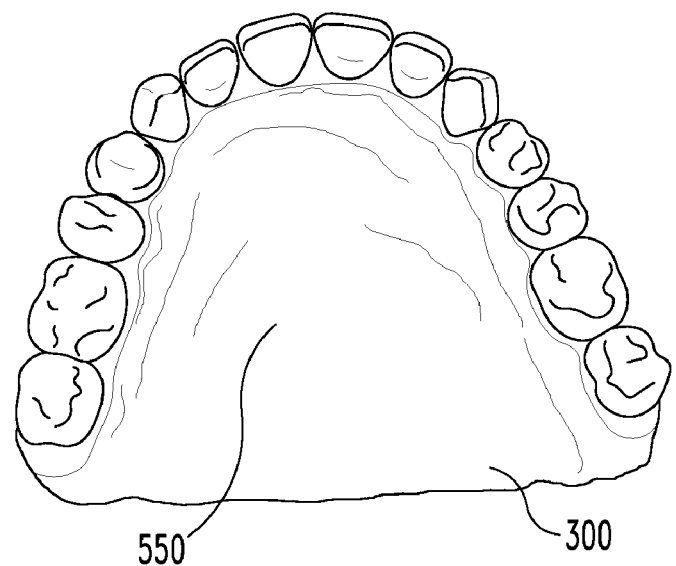
FIG. 25 is a bottom view of one embodiment of a pre-manufactured upper denture.

For the upper pre-manufactured denture 300 having a flexible palate (shown in FIG. 25), the dentist can contour the flexible palate to fit the patient's palate or roof of mouth. In one embodiment, for the palate made of wax, the dentist can warm the wax and then move and/or shape the wax to replicate the patient's palate. In another embodiment, for a patient with a high palate, the dentist may place impression material onto the flat palate or between the wax and the upper base plate to fill in the space created between the palate and the roof of the patient's mouth to create a snug fit between the upper pre-manufactured denture 300 and the roof of the patient's mouth. The impression material may be any type of durable flexible material suitable for forming an impression of a patient's mouth. By contouring the flexible palate to fit the patient's palate, less impression material will be required, as described below. Beneficially, less impression material may result in a lower cost to fit the upper pre-manufactured denture 300 to a patient's palate. Similarly, less impression material may result in a more pleasant experience for the patient since there will be less impression material in the patient's mouth when the dentist takes an impression of the patient's upper arch and prosthetic teeth, as described below.

Figure 26:
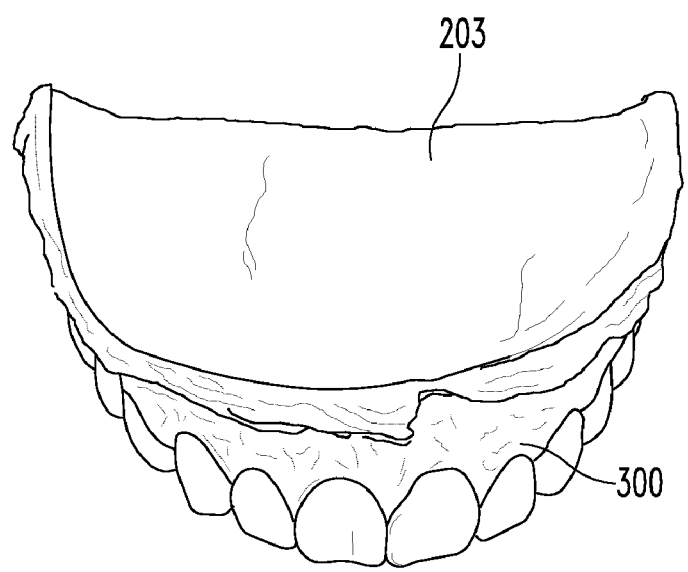
FIGS. 26-37 are perspective views of one embodiment of a method of relining a pre-manufactured denture.

The dentist fills the upper pre-manufactured denture 300 with impression material 203 as shown in FIG. 26. Next, the dentist takes a reline impression 400 of the patient's arch by using the upper pre-manufactured denture 300 filled with impression material 203 as a custom tray and inserting the upper pre-manufactured denture 300 into a patient's mouth and pressing upwardly against the patient's upper gum.

In one embodiment, the dentist determines the bite relation of the upper prosthetic teeth to the lower prosthetic teeth by using both the upper pre-manufactured denture 300 filled with impression material 203 and the lower pre-manufactured denture filled with impression material 203 and pressing the pre-manufactured dentures into the patient's gums. Preferably, the upper pre-manufactured denture 300 and the lower pre-manufactured denture occlude and the prosthetic teeth fit together properly when the patient closes his jaws. In this embodiment, the patient will close his upper pre-manufactured denture 300 and lower pre-manufactured denture together. The dentist will check the bite of the patient as the patient repeatedly opens and closes his jaw. The dentist removes the upper pre-manufactured denture 300 and the lower pre-manufactured denture from the patient's mouth.

Figure 27:
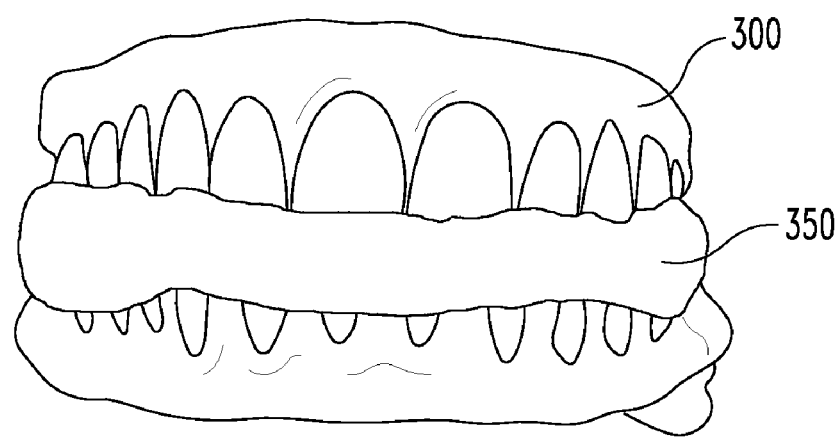

In another embodiment, illustrated in FIG. 27, the dentist uses a pre-manufactured bite registration 350 to ensure the proper occlusion, and the upper pre-manufactured denture 300 and the lower pre-manufactured denture fit together properly when the patient closes his jaw. Next, the dentist fits the pre-made bite registration 350 onto the upper pre-manufactured denture 300. The dentist also fills the lower pre-manufactured denture with impression material 203 and presses the lower pre-manufactured denture onto the patient's lower gums. The dentist pushes the prosthetic teeth of the lower pre-manufactured denture into the bite registration 350 as the patient closes his mouth and bites his prosthetic teeth in the upper pre-manufactured denture 300 and lower pre-manufactured denture together.

Figure 28:
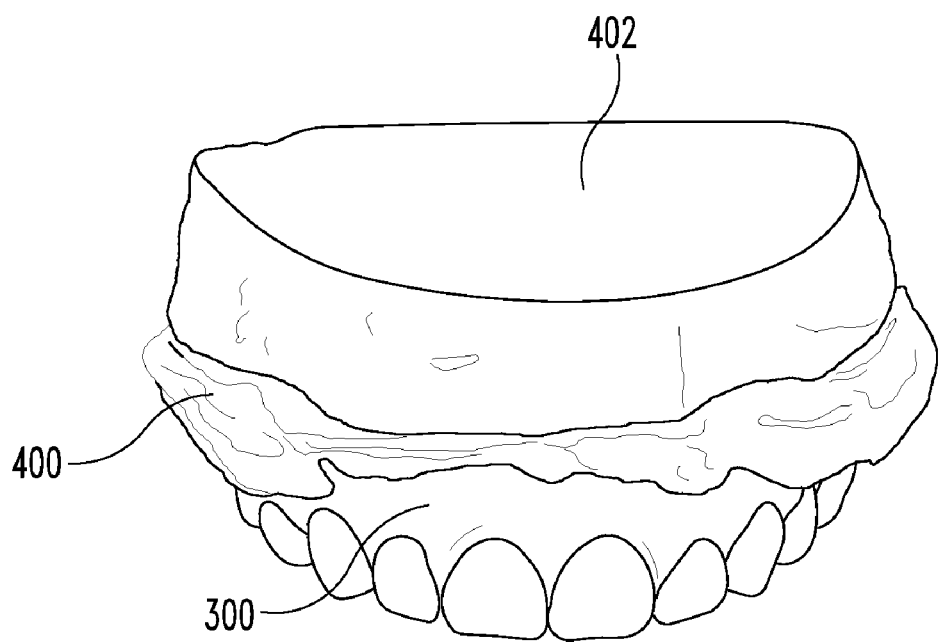

The dentist pours dental stone in the reline impression 400 to make a dental stone model 402 of the arch as shown in FIG. 28. After a period of time, the dental stone model 402 hardens.

Figure 29:
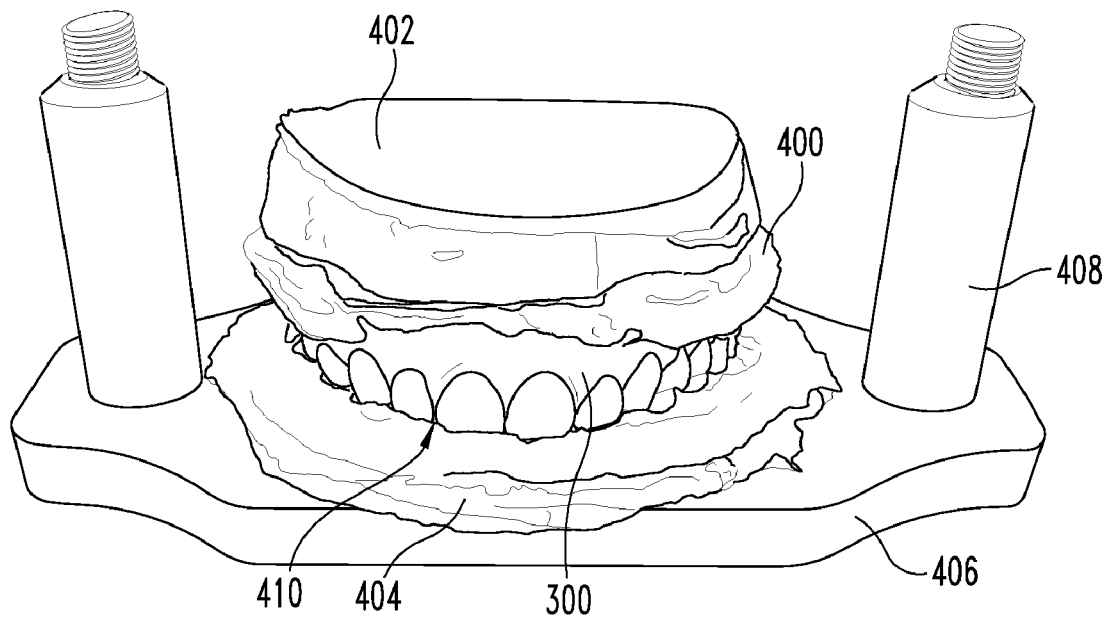

A plaster patty 404 is formed on a lower half 406 of a reline jig 408 as shown in FIG. 29. In other embodiments, other types of material may be substituted for the plaster patty 404, such as plastic, polymer, or ceramic. The prosthetic teeth are pressed into the patty 404 until an impression 410 of the cusps of prosthetic teeth is formed. In one form, the prosthetic teeth remain in the patty 404 until the patty 404 hardens.

Figure 30:
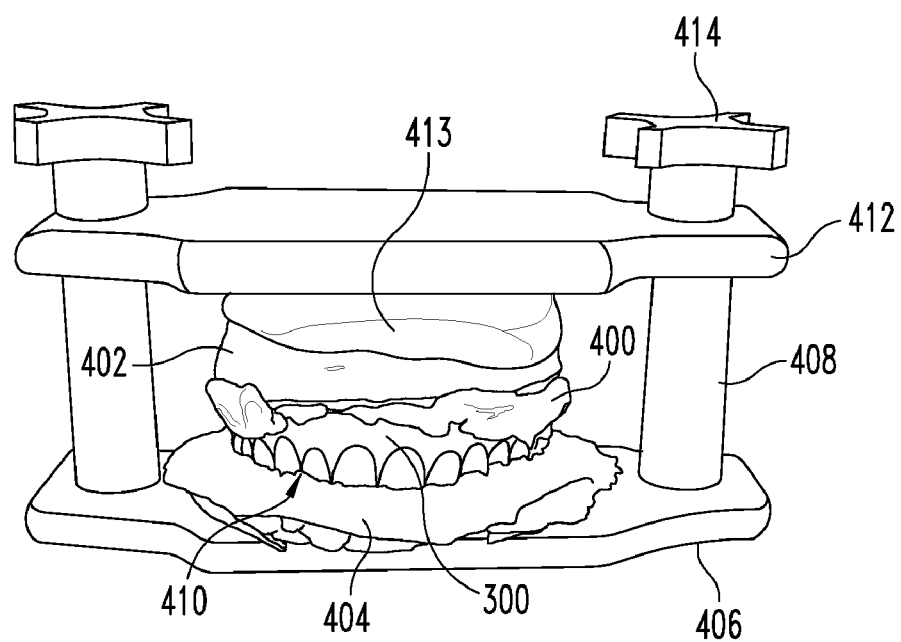

As shown in FIG. 30, the reline jig 408 includes an upper half 412. Dental plaster 413 is placed on the dental stone model 402, and the upper half 412 is placed on top of the dental plaster 413. In one form, a nut 414 is placed on the upper half 412 of the reline jig 408 and twisted to compress the dental plaster 413 onto the dental stone model 402. In other embodiments, other forms of pressing the upper half 412 and the lower half 406 of the reline jig 408 to press the dental plaster 413 onto the dental stone model 402 may be used. The reline jig 408 is positioned in a certain configuration due to the thickness of the reline impression 400 while the dental plaster 413 hardens.

Figure 31:
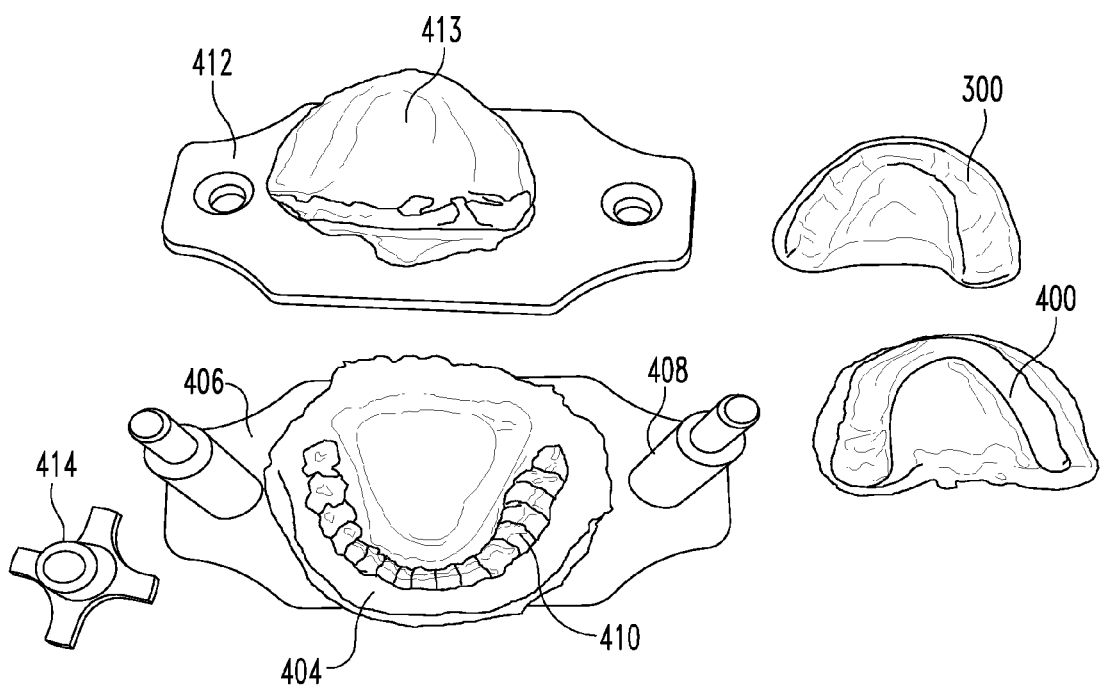

After the dental plaster 413 hardens, the upper half 412 is removed from the reline jig 408. The upper pre-manufactured denture 300 is removed from the dental plaster 413. The reline impression 400 is removed from the upper pre-manufactured denture 300 as shown in FIG. 31. The upper pre-manufactured denture 300 is cleaned to remove any parts of the reline impression 400 and the dental plaster 413 that may have become stuck on the upper pre-manufactured denture 300.

Figure 32:
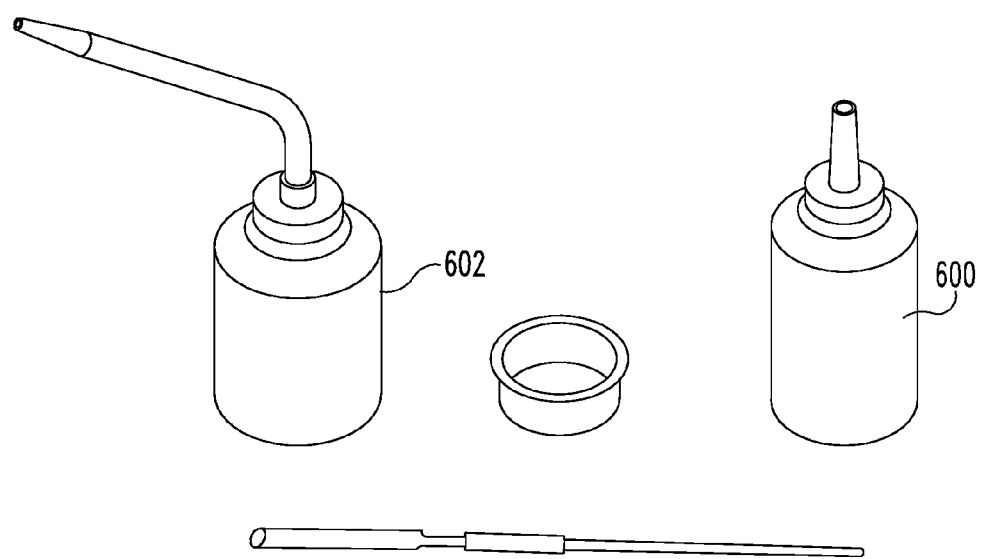
Figure 33:
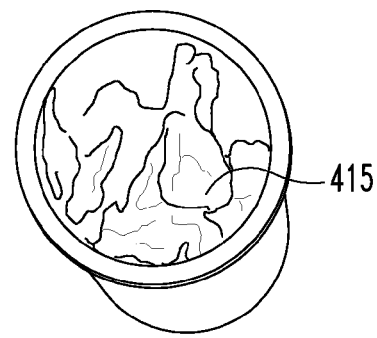
Figure 34:
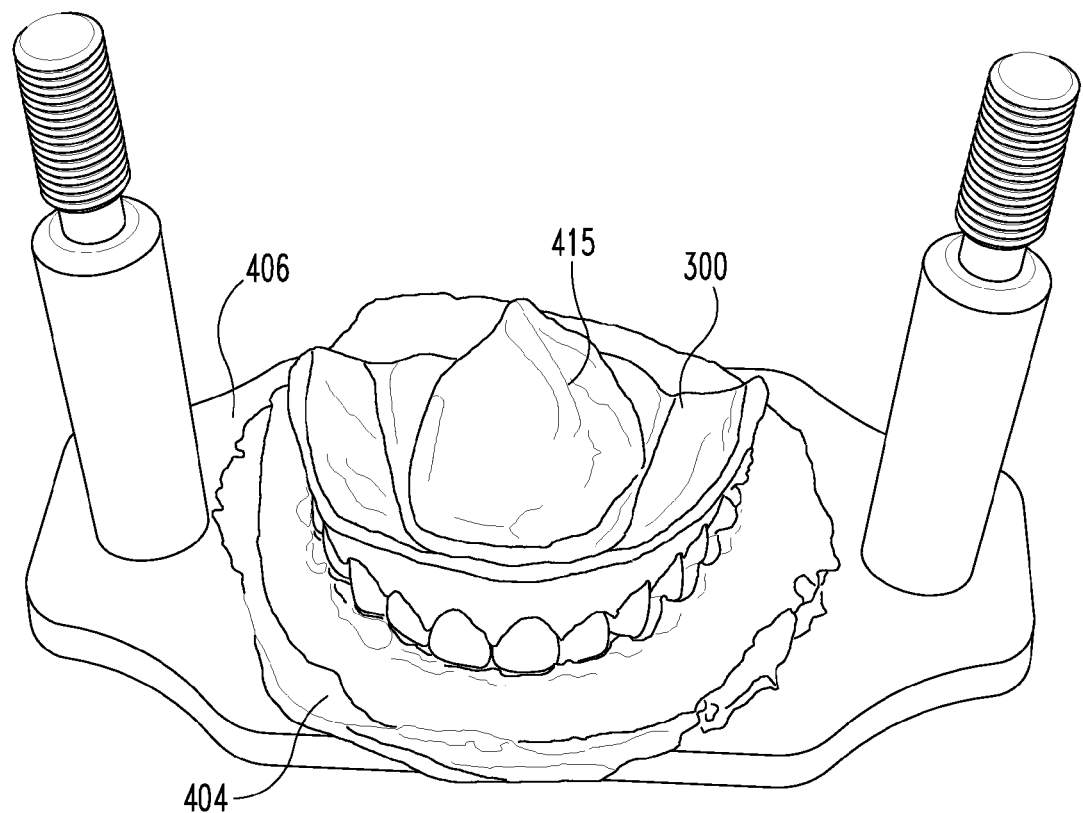

The upper pre-manufactured denture 300 is placed on the patty 404 which remains on the lower half 406 of the reline jig 408. Amounts of acrylic 600 and monomer 602 as shown in FIG. 32 are measured and then mixed together and stirred until a doughy state is reached to form packing material 415 as shown in FIG. 33. The mixture of acrylic 600 and monomer 602 or packing material 415 is packed into the tissue side of the upper pre-manufactured denture 300 as shown in FIG. 34. A cold cure type acrylic or heat cure type of acrylic may be used. Additionally, other colors of acrylic may be used.

Figure 35:
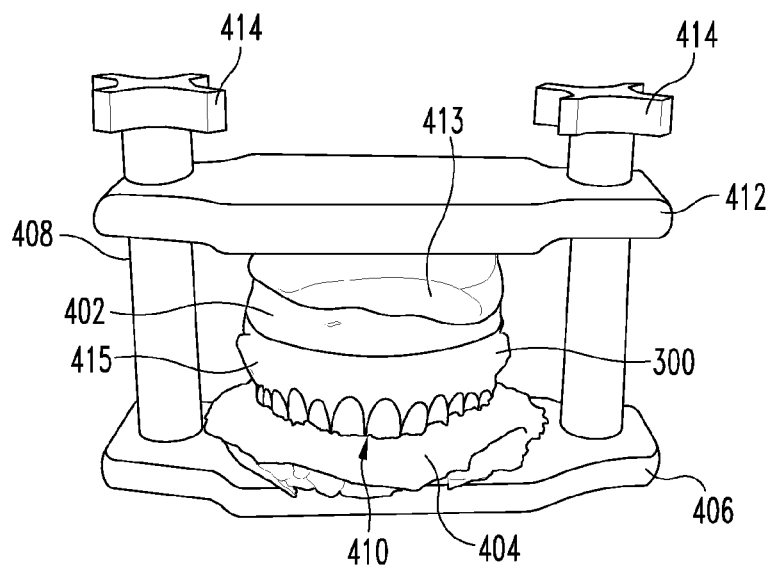

The dental stone model 402 and dental plaster 413 are placed on top of the mixture of acrylic and monomer or packing material 415 as shown in FIG. 35. As shown in FIG. 35, preferably the dental stone model 402 and dental plaster 413 are stuck together as one piece. The upper half 412 of the reline jig 408 is placed on top of the dental plaster 413. In one form, a pair of nuts 414 is placed on the upper half 412 of the reline jig 408 and each nut is twisted to compress the packing material 415 as shown in FIG. 35; however, other forms of compressing the upper half 412 and the lower half 406 may be used. The reline jig 408 is set to the certain configuration used previously to press the upper half 412 onto the lower half 406 to press the dental plaster 413 onto the dental stone model 402. This certain configuration will ensure the correct amount of packing material 415 adheres to the pre-manufactured denture to create a reline pre-manufactured denture and any excess packing material 415 will be squeezed out as the upper half 412 and the lower half 406 are pressed together.

Figure 36:
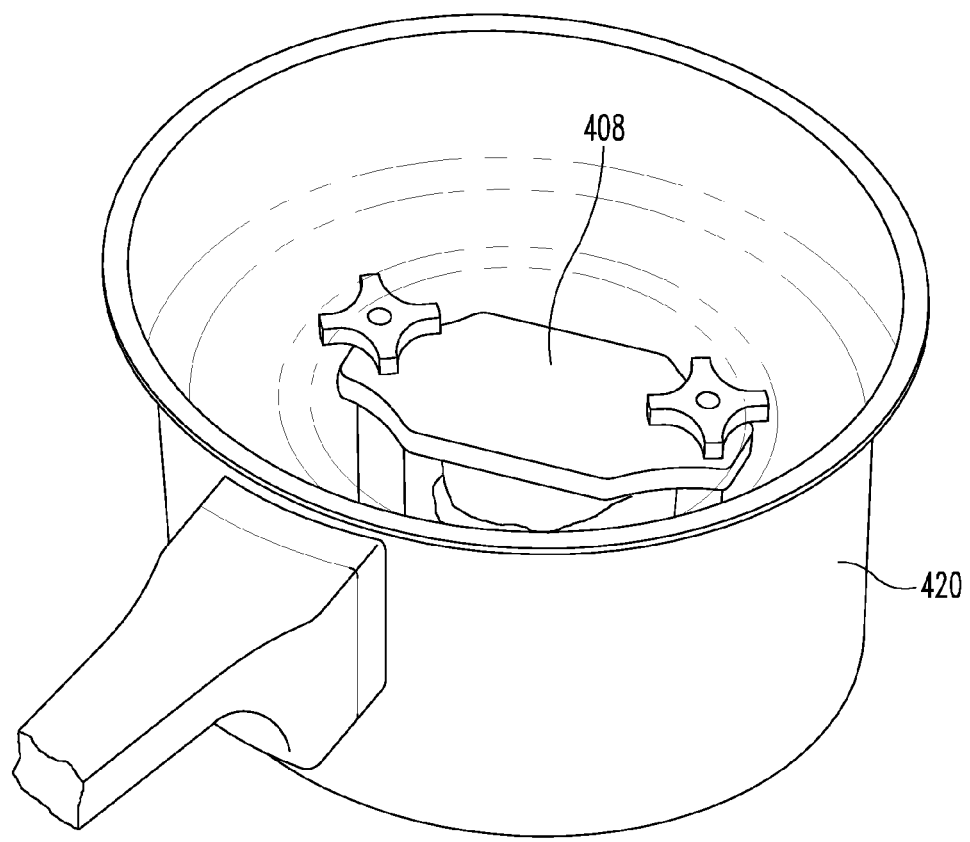

The reline jig 408 is placed in a hot water pressure pot 420 as shown in FIG. 36. The pressure pot 420 typically is sealed and has a valve on it so the dental technician can add compressed air. The packing material 415 cures in the pressure pot 420 to form the upper reline pre-manufactured denture 450. The reline jig 408 is removed from the pressure pot 420, and the upper half 412 is removed from the jig 408. The dental stone model 402 is also removed from the upper reline pre-manufactured denture 450 which is now a custom fit denture. Similarly, a lower reline pre-manufactured denture 452 can also be formed using this method.

Figure 37:
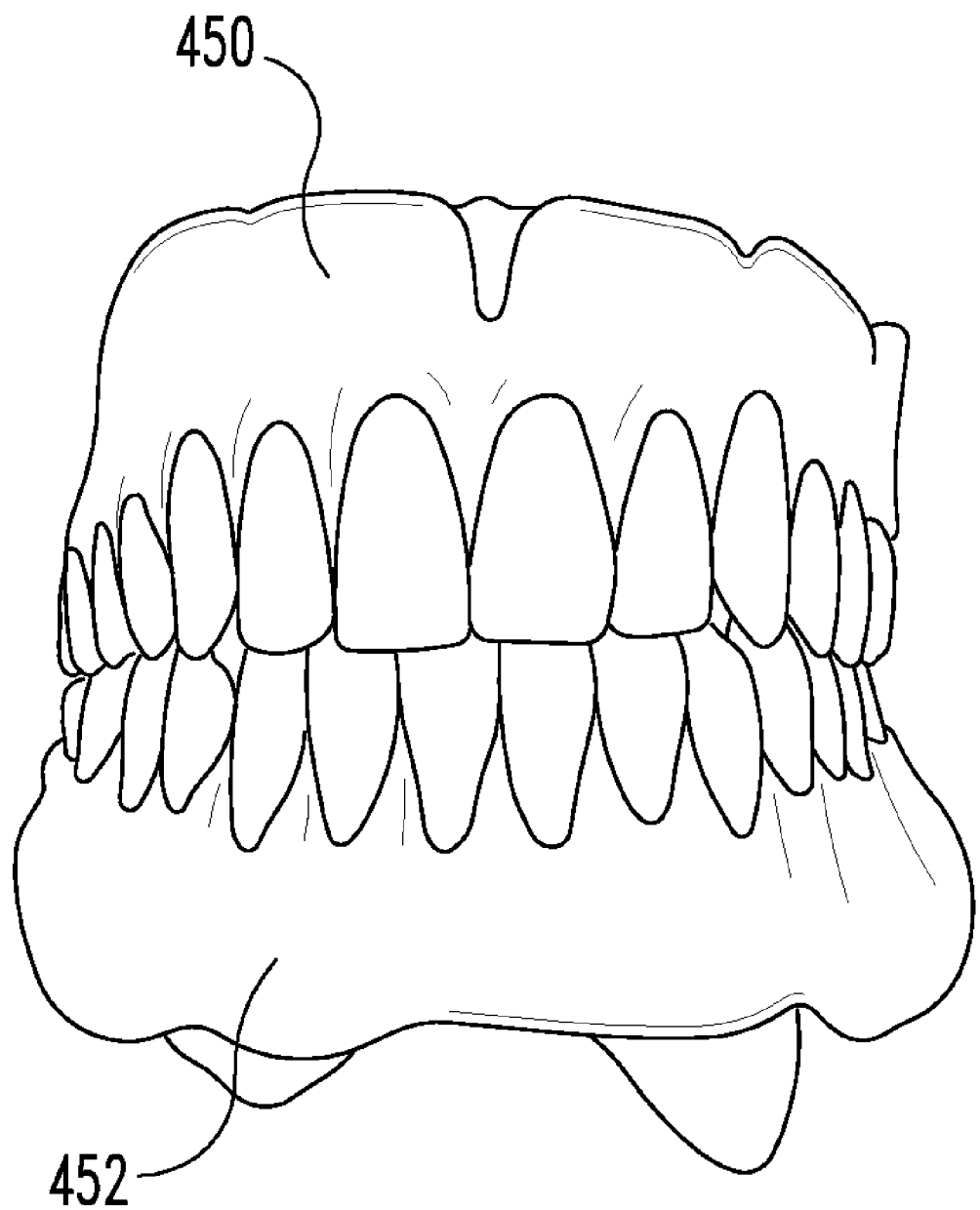

Optionally, the upper reline pre-manufactured denture 450 and lower reline pre-manufactured denture 452 are finished to remove any burrs, bubbles, or other imperfections from the acrylic, and the upper reline pre-manufactured denture 450 and lower reline pre-manufactured denture 452 can be shined with denture polish. The upper reline pre-manufactured denture 450 and lower reline pre-manufactured denture 452 are shown in FIG. 37.

Preferably, at a second visit the dentist tests the fit of the upper reline pre-manufactured denture 450 and the lower reline pre-manufactured denture 452 in the patient's mouth. In one form, the dentist may adjust the upper reline pre-manufactured denture 450 and/or the lower reline pre-manufactured denture 452 by removing a portion of the acrylic such that the upper reline pre-manufactured denture 450 and/or the lower reline pre-manufactured denture 452 fits the medical patient's mouth and gums better.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of manufacturing a denture comprising:
    forming a dental matrix by removing a master denture from a denture container filled with a hard dental material and an impression material to expose an impression of a plurality of prosthetic teeth in said impression material created from said master denture;
    forming a standard sized denture from said dental matrix by placing a plurality of prosthetic teeth in said impression, covering said plurality of prosthetic teeth with a doughy material, and curing said doughy material to create said standard sized denture; and
    lining said standard sized denture to form a custom fit denture for a medical patient by filling said standard sized denture with an impression material, placing said standard sized denture in said medical patient's oral cavity to capture an impression of said medical patient's arch, placing said standard sized denture filled with said impression in a reline jig, removing said impression from said standard sized denture, filling said standard sized denture with a packing material, and curing said packing material in said reline jig wherein said impression determines a certain configuration of said reline jig to form said custom fit denture.

2. The method of claim 1, wherein said step of forming a dental matrix further comprises:
    covering said master denture having a plurality of prosthetic teeth with a layer of said doughy material;
    placing said master denture covered with said doughy material in said denture container;
    filling said denture container with a fluent curable dental material to cover said master denture and said layer of doughy material with said fluent dental material;
    curing said fluent dental material in said denture container over a period of time to form said hard dental material; and
    removing said master denture from said denture container to expose said impression formed from said plurality of prosthetic teeth in said layer of doughy material to create said dental matrix.

3. The method of claim 2, further comprising:
    removing said dental matrix from said denture container; and
    creating a subsequent dental matrix in said denture container by using said master denture or a subsequent denture.

4. The method of claim 2, wherein said master denture is a master upper denture and said dental matrix is an upper dental matrix; and
    said step of covering said master upper denture with said layer of doughy material includes packing said doughy material into a tissue side of said master upper denture to form a substantially flat palate on said tissue side.

5. The method of claim 1, wherein said step of forming a dental matrix further comprises:
    filling a cavity with said impression material, wherein said denture container includes an upper plate and a lower plate, said upper plate having said master denture attached thereto, and said lower plate defining said cavity;
    positioning said master denture in said cavity filled with said impression material;
    curing said impression material in said cavity over a period of time to form said hard dental material, said hard dental material substantially resistant to degradation; and
    removing said master denture from said cavity to expose said impression formed from said plurality of prosthetic teeth in said hard dental material to create said dental matrix.

6. The method of claim 5, wherein said impression material is silicone.

7. The method of claim 5, wherein said step of filling said cavity includes filling a plurality of cavities, said upper plate having a plurality of master dentures attached thereto, and said lower plate defining a plurality of cavities.

8. The method of claim 1, wherein said filling said standard sized denture includes filling an upper standard sized denture and a lower standard sized denture with amounts of impression material; and
    occluding said upper standard sized denture and said lower standard sized denture by pressing said upper standard sized denture filled with said impression material and said lower standard sized denture filled with said impression material into a pre-manufactured bite registration while said upper standard sized denture and said lower standard sized denture are each positioned on said medical patient's arches.

9. A method of forming a custom fit denture from a standard sized denture for a medical patient, comprising:
filling a standard sized denture with an amount of impression material;
creating impression of a medical patient's arch in said standard sized denture filled with said impression material;
placing said standard sized denture filled with said impression in a reline jig;
removing said impression from said standard sized denture;
filling said standard sized denture with a packing material;
placing said standard sized denture filled with said packing material in said reline jig;
adjusting said reline jig to said certain configuration determined by said impression; and
curing said packing material in said standard sized denture to form a custom fit denture for said medical patient.

10. The method of claim 9, wherein said filling said standard sized denture includes filling an upper standard sized denture and a lower standard sized denture with amounts of said impression material; and
occluding said upper standard sized denture and said lower standard sized denture by pressing said upper standard sized denture filled with said impression material and said lower standard sized denture filled with said impression material into a pre-manufactured bite registration while said upper standard sized denture and said lower standard sized denture are each positioned on said medical patient's arches.

11. The method of claim 9, further comprising:
wherein said step of curing includes placing said reline jig in a hot water pressure pot, said pot sealed and configured to receive compressed air.

12. The method of claim 9, further comprising:
polishing said custom fit denture.

13. The method of claim 9, further comprising:
adjusting said custom fit denture to fit an oral cavity of said medical patient.

* * * * *